United States Patent
Chang et al.

(10) Patent No.: US 12,215,127 B2
(45) Date of Patent: Feb. 4, 2025

(54) COMPOSITIONS AND METHODS FOR PROFILING OF GUT MICROBIOTA-ASSOCIATED BILE SALT HYDROLASE (BSH) ACTIVITY

(71) Applicant: CORNELL UNIVERSITY, Ithaca, NY (US)

(72) Inventors: Pamela Chang, Ithaca, NY (US); Bibudha Parasar, Ithaca, NY (US); Lin Han, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 279 days.

(21) Appl. No.: 17/231,432

(22) Filed: Apr. 15, 2021

(65) Prior Publication Data
US 2021/0323996 A1    Oct. 21, 2021

Related U.S. Application Data

(60) Provisional application No. 63/011,449, filed on Apr. 17, 2020.

(51) Int. Cl.
C07J 43/00       (2006.01)
G01N 33/68       (2006.01)

(52) U.S. Cl.
CPC ........ *C07J 43/003* (2013.01); *G01N 33/6848* (2013.01); *G01N 2333/98* (2013.01); *G01N 2800/065* (2013.01)

(58) Field of Classification Search
CPC ............. C07J 43/003; G01N 2800/065; G01N 33/6848; G01N 2333/98
See application file for complete search history.

(56) References Cited

U.S. PATENT DOCUMENTS

| | | |
|---|---|---|
| 2002/0151526 A1 | 10/2002 | Gallop et al. |
| 2006/0030551 A1 | 2/2006 | Bhat et al. |
| 2007/0059246 A1 | 3/2007 | Cavagna et al. |
| 2016/0176917 A1 | 6/2016 | Wang et al. |
| 2016/0289262 A1 | 10/2016 | Wang et al. |
| 2016/0311848 A1 | 10/2016 | Sudhir et al. |
| 2018/0319836 A1 | 11/2018 | Yu et al. |
| 2018/0371009 A1 | 12/2018 | Pellicciari et al. |

FOREIGN PATENT DOCUMENTS

| | | |
|---|---|---|
| EP | 0259185 A1 | 3/1988 |

OTHER PUBLICATIONS

Mullish et al., Functional microbiomics: Evaluation of gut microbiota-bile acid metabolism interactions in health and disease. Methods, vol. 149, pp. 49-58 (Year: 2018).*

Massarenti et al., Fluorous-tag assisted synthesis of bile acid-bisphossphonate conjugates via orthogonal click reactions: an access to potential anti-resorption bone drugs. Organic & Biomolecular Chemistry, vol. 15, pp. 4907-4920 (Year: 2017).*

Adhikari, A.A., et al., "Development of a covalent inhibitor of gut bacterial bile salt hydrolases", Nature Chemical Biology, Mar. 2020, pp. 318-326, vol. 16.

Kato, D., et al., "Activity-based probes that target diverse cysteine protease families", Nature Chemical Biology, Published online May 24, 2005, Jun. 2005, pp. 33-38, vol. 1, No. 1.

Parasar, B., et al., "Chemoproteomic Profiling of Gut Microbiota-Associated Bile Salt Hydrolase Activity", ACS Central Science, Published Apr. 18, 2019, pp. 867-873, 875.

* cited by examiner

*Primary Examiner* — Barbara P Badio
(74) *Attorney, Agent, or Firm* — Scully, Scott, Murphy & Presser, P.C.

(57) ABSTRACT

A composition having the following structure:

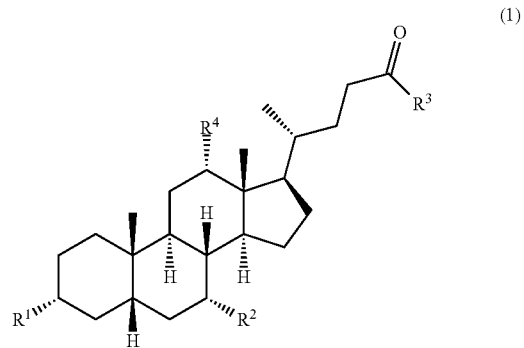

wherein: $R^1$ is OH, ester group, ether group, amine, thiol, thioether, halide, or a group containing an alkynyl or azido functionality; $R^2$ is H, OH, ester group, ether group, amine, thiol, thioether, halide, or a group containing an alkynyl or azido functionality; $R^3$ is a group containing a reactive functionality capable of covalent binding to a thiol or amine; and $R^4$ is H, OH, ester group, ether group, amine, thiol, thioether, halide, or a group containing an alkynyl or azido functionality; wherein one of $R^1$, $R^2$ and $R^4$ is a group containing an alkynyl or azido functionality. Also disclosed is a method for profiling changes in BSH enzyme activity by attaching active BSH enzymes in a sample to the probe shown above, attaching a tag to the probe, and detecting the active BSH enzymes to obtain an activity profile.

25 Claims, 18 Drawing Sheets
(5 of 18 Drawing Sheet(s) Filed in Color)
Specification includes a Sequence Listing.

2A
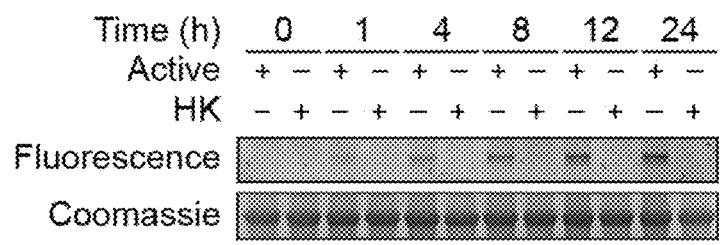
2B
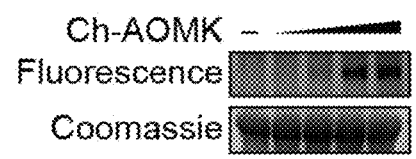
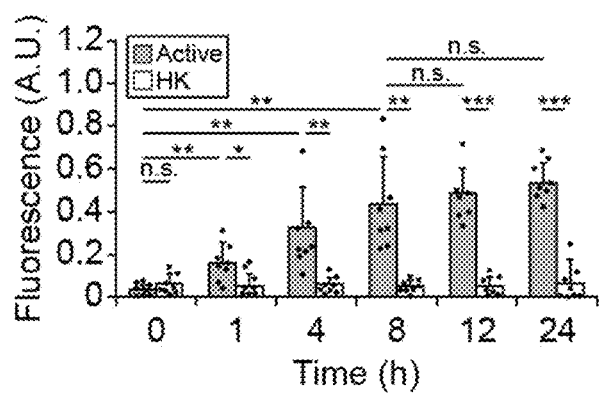
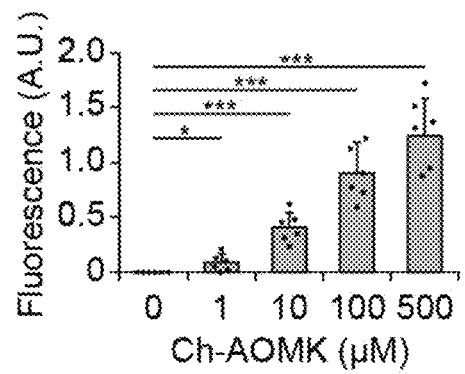
FIGS. 2A-2B

13A 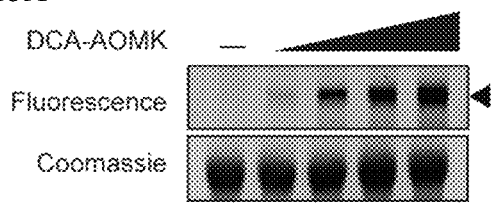 13B 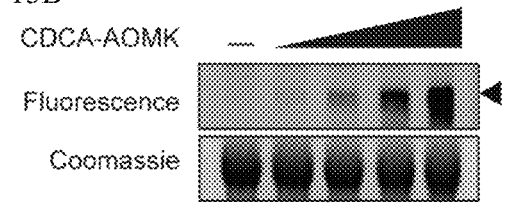
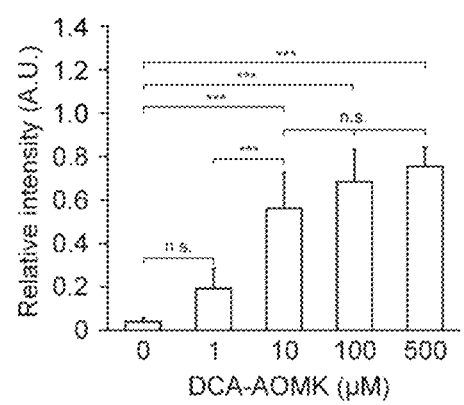 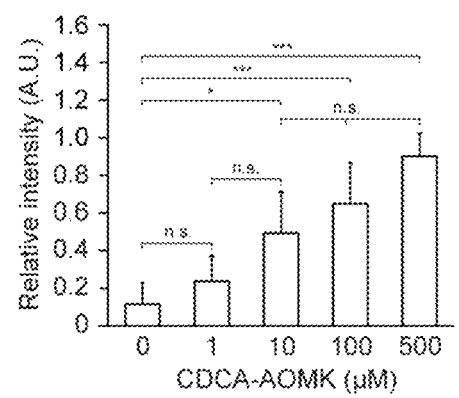
FIGS. 13A-13B

COMPOSITIONS AND METHODS FOR PROFILING OF GUT MICROBIOTA-ASSOCIATED BILE SALT HYDROLASE (BSH) ACTIVITY

CROSS REFERENCE TO RELATED APPLICATION

This application claims the benefit of priority from U.S. Provisional Application No. 63/011,449, filed on Apr. 17, 2020.

GOVERNMENT SUPPORT

This invention was made with government support under Grant No. GM133501. The government has certain rights in the invention.

INCORPORATION BY REFERENCE OF SEQUENCE LISTING

The Sequence Listing in the ASCII text file, named as 38273_9358_02_US_SequenceListing.txt of 2 KB, created on May 26, 2021, and submitted to the United States Patent and Trademark Office via EFS-Web, is incorporated herein by reference.

FIELD OF THE INVENTION

The invention generally relates to methods for detecting or profiling activities of bile salt hydrolases (BSHs) in a subject. The invention more particularly relates to the use of bile acid-based probes containing a detectable marker or affinity probe for detecting or profiling activities of BSHs. The invention furthermore relates to using such activity information to identify markers of metabolic disorders related to BSHs, such as inflammatory bowel diseases (MDs).

BACKGROUND OF THE INVENTION

The gateway reaction of secondary bile acid biosynthesis is mediated by bile salt hydrolases (BSHs), bacterial cysteine hydrolases whose action precedes other bile acid modifications within the gut. To assess how changes in bile acid metabolism mediated by certain intestinal microbiota impact gut physiology and pathobiology, methods are needed to directly examine the activities of BSHs because they are master regulators of intestinal bile acid metabolism. Such methods would be particularly important for profiling and identifying BSH activity markers associated with inflammatory bowel disease (IBD), colitis, or Crohn's Disease. Nevertheless, such methods have thus far remained elusive.

Bile acids (BAs) are important metabolites that are initially produced by the host and are subsequently chemically diversified by the gut microbiota. First, so-called primary BAs are synthesized from cholesterol by hepatocytes in the liver to produce saturated, hydroxylated C24 cyclopentanephenanthrene sterols, such as cholic acid and chenodeoxycholic acid. These free BAs are further modified in the liver to increase water solubility by conjugation of the carboxylic acid to glycine or taurine. The conjugated BAs are then actively secreted into bile and stored in the gall bladder. During digestion, bile is released into the small intestine, where the conjugated BAs act as detergents to solubilize dietary lipids and lipid-soluble vitamins.

In the small intestine, conjugated BAs are metabolized by bile salt hydrolase (BSH) enzymes expressed by the gut microbiota via hydrolysis at the C24 amide bond to release unconjugated BAs. The BSH-catalyzed step is considered the "gateway reaction" of microbiota-mediated bile salt metabolism because deconjugation needs to occur before all other transformations affected by the gut microbiome. These include dehydroxylation, dehydrogenation, and sulfation, leading to a large collection of so-called secondary BAs, which have direct effects on the microbiota and also mediate many important biological processes, including host metabolism and immune regulation. Thus, BSHs are bacterial enzymes that produce critical metabolites necessary for the proper physiological function of the gut. Despite the significance of these enzymes, their functions in the gut are not well understood due in part to a lack of tools to assess their activities.

SUMMAKY OF THE INVENTION

The present disclosure describes methods for profiling and identifying activities of BSHs, such as by use of chemoproteomic tools, to profile changes in microbiome-associated BSH activity, particularly from the standpoint of identifying markers associated with disorders which implicate BSH activity, e.g., IBD, colitis, Crohn's Disease, metabolic syndrome, or obesity. Such profiling can be used as a diagnostic test for one or more of the foregoing diseases or other diseases (e.g., cancer or microbial infection).

In a first aspect, the present disclosure is directed to a probe composition that covalently binds to BSH and which includes a reactive group for subsequent linkage of a tag (e.g., detectable label or affinity probe) that can be used for detection and profiling of the BSH in a chemoproteomic testing method, such as electrophoresis, in situ gel imaging, or enrichment by pull-down method followed by proteomic characterization, such as by mass spectroscopy. The activity of the BSH can also be elucidated by, for example, Western Blot. The detectable label may be, for example, a fluorophore, such as any of the organic or inorganic (e.g., quantum dot) fluorophores of the art. The affinity probe may be any molecule known to form an affinity bond with another molecule (e.g., biotin, avidin, streptavidin, or antibody).

The probe composition has the following structure:

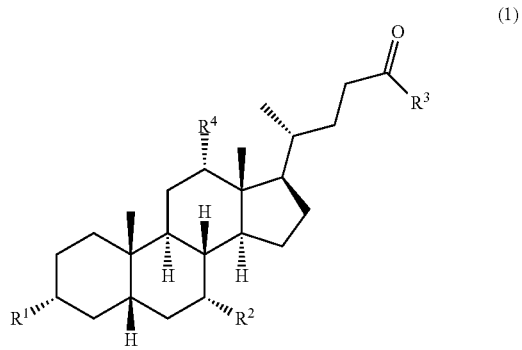

(1)

wherein: $R^1$ is OH, ester group, ether group, amine, thiol, thioether, halide, or a group containing an alkynyl or azido functionality; $R^2$ is H, OH, ester group, ether group, amine, thiol, thioether, halide, or a group containing an alkynyl or azido functionality; $R^3$ is a group containing a reactive functionality capable of covalent binding to a thiol or amine;

and R⁴ is OH, ester group, ether group, amine, thiol, thio-ether, halide, or a group containing an alkynyl or azido functionality; wherein one of R¹, R² and R⁴ is a group containing an alkynyl or azido functionality. In particular embodiments, R¹ is a group containing an alkynyl or azido functionality; R² is H or OH; R³ is a group containing a reactive functionality capable of covalent binding to a thiol or amine; and R⁴ is H or OH.

The probe composition of Formula (1) binds to the BSH via functional group R³. Once the probe composition of Formula (1) is bound to active BSH enzyme, a tag (e.g., a detectable marker or affinity probe) can be covalently attached to the composition of Formula (1) using Cu-catalyzed "click" chemistry. Alternatively, the tag may be first attached to the probe composition of Formula (1), and the tagged version of Formula (1) covalently bound to the BSH enzyme. The tagged version of Formula (1) may have the following structure:

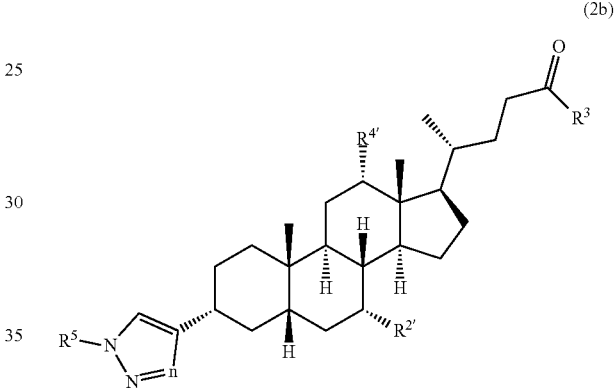

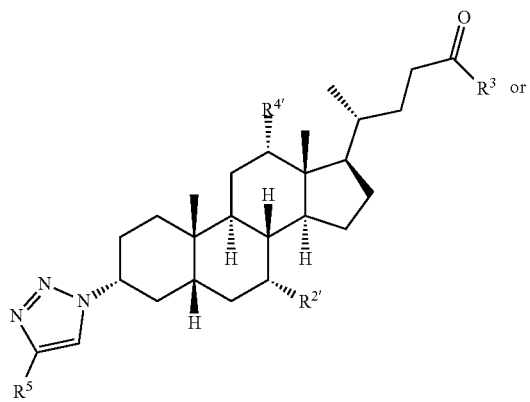

wherein: $R^{1'}$ is OH, ester group, ether group, amine, thiol, thioether, halide, or a group $R^a$; $R^{2'}$ is H, OH, ester group, ether group, amine, thiol, thioether, halide, or a group $R^a$; $R^3$ is a group containing a reactive functionality capable of covalent binding to a thiol or amine; and $R^{4'}$ is H, OH, ester group, ether group, amine, thiol, thioether, halide, or a group $R^a$; wherein one of $R^{1'}$, $R^{2'}$ and $R^{4'}$ is a group $R^a$, wherein $R^a$ is

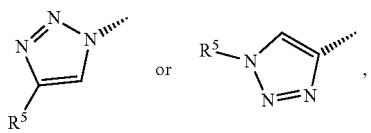

and $R^5$ is the tag (e.g., detectable marker or affinity probe) useful for detecting BSH active enzyme.

Some more specific examples of tagged versions of Formula (1) include the following structures:

wherein: $R^{2'}$ is H, OH, ester group, ether group, amine, thiol, thioether, or halide; $R^3$ is a group containing a reactive functionality capable of covalent binding to a thiol or amine; $R^{4'}$ is H, OH, ester group, ether group, amine, thiol, thioether, or halide; and $R^5$ is a group containing a tag (e.g., detectable marker or affinity probe). In more particular embodiments, $R^{2'}$ is H or OH; $R^3$ is a group containing a reactive functionality capable of covalent binding to a thiol or amine; $R^{4'}$ is H or OH; and $R^5$ is a tag.

In another aspect, the present disclosure is directed to a method for profiling changes in gut microbiome-associated BSH activity in an organism (e.g., mammal or vertebrate), comprising: (i) obtaining a biological sample containing active and inactive BSH enzyme from the organism; (ii) selectively attaching the active BSH enzymes in the obtained sample to a BSH activity-based probe ("probe") according to Formula (1), via $R^3$ of the probe, to provide a probe-BSH enzyme conjugate (labeled BSH enzyme); (iii) attaching, by click chemistry, a tagging molecule to an alkynyl or azido group of the probe of Formula (1) after the probe has attached to the BSH enzyme, to result in a tag-BSH enzyme conjugate, wherein the tag is useful for detecting the BSH enzyme; and (iv) detecting the tagged active BSH enzymes to obtain a BSH enzyme activity profile of the organism; wherein the tagged BSH activity-based probe produced in step (iii), while attached to active BSH enzyme, has the following structure:

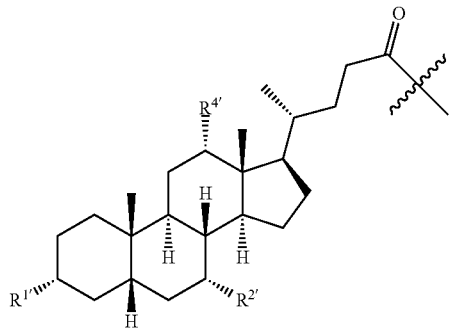

(3)

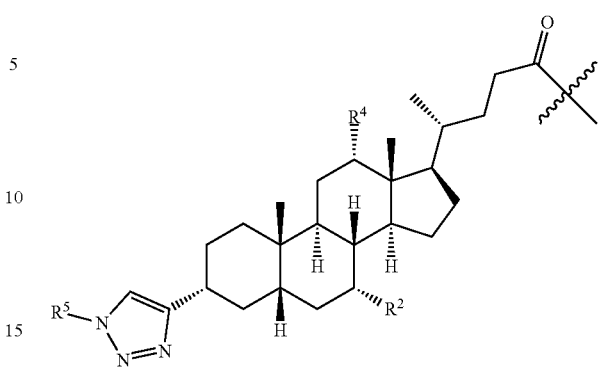

(3b)

wherein: $R^{1'}$ is OH, ester group, ether group, amine, thiol, thioether, halide, or a group $R^a$; $R^{2'}$ is H, OH, ester group, ether group, amine, thiol, thioether, halide, or a group $R^a$; $R^{4'}$ is H, OH, ester group, ether group, amine, thiol, thioether, alkynyl, azido, or a group $R^a$; wherein one of $R^{1'}$, $R^{2'}$ and $R^{4'}$ is $R^a$, wherein $R^a$ is

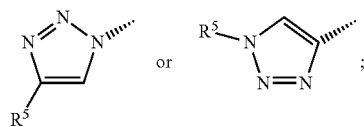

$R^5$ is the tag useful for detecting the BSH enzyme; and the wavy line indicates a direct or indirect covalent bond to the active BSH enzyme obtained from the organism.

In some embodiments, the tag-BSH enzyme conjugate has one of the following more specific structures:

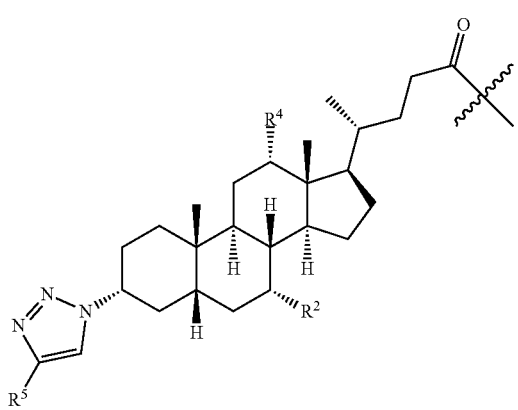

(3a)

wherein: $R^2$ and $R^4$ are as defined above, or more particularly, $R^2$ is H or OH; $R^4$ is H or OH; $R^5$ is a tag (i.e., detectable marker or affinity probe); and the wavy line indicates a direct or indirect covalent bond to the active BSH obtained from the gut of the organism.

The attaching step (ii) may be achieved by a two-step method as follows:

(a) contacting the obtained sample with a BSH activity-based probe according to Formula (1) to result in binding of the BSH activity-based probe (via $R^3$ in Formula 1) to active BSH enzymes in the obtained sample to provide labeled BSH enzymes (i.e., labeled with a group containing an alkynyl or azido functionality in any one of $R^1$, $R^2$, or $R^4$ in Formula 1), wherein $R^3$ in Formula (1) forms a covalent bond with a thiol or amine of the active BSH enzymes in the obtained sample to form the labeled BSH enzymes; and (b) contacting the labeled BSH enzymes with a tagging molecule (i.e., molecule that contains a detectable marker or affinity probe and counterpart click chemistry functionality) that attaches to the BSH activity-based probe, as already attached to the BSH enzyme via $R^3$, to provide a tagged BSH enzyme. In particular embodiments, the activity-based probe (as attached to the BSH enzyme) that has been tagged has the structure shown in Formula (3), or more particularly, Formula (3a) or (3b).

In a second embodiment, the attaching step (ii) is achieved by a one-step method in which the obtained sample is contacted with a detectably labeled BSH activity-based probe to provide detectably labeled BSH enzyme, wherein the detectably labeled BSH activity-based probe has the structure of Formula (2), or more particularly, Formula (2a) or (2b).

In any of the above disclosed methods, the method may function as a diagnostic test for colitis in the organism, wherein the colitis may be, more particularly, inflammatory bowel disease (IBD), ulcerative colitis, or Crohn's disease.

The present disclosure is also directed to a kit for labeling an active BSH enzyme with a probe and making the probe detectable. The kit includes: i) the composition of Formula (1), which functions as a probe for the active BSH enzyme by covalently binding the composition of Formula (1) to the active BSH enzyme via $R^3$, and ii) a molecule that contains a detectable marker or affinity probe, wherein the molecule forms a covalent bond with $R^1$ in Formula (1) after the composition of Formula (1) is bound to the active BSH enzyme. The kit may also further include: iii) instructions for attaching the composition of Formula (1) to an active BSH enzyme and instructions for attaching the molecule containing the detectable marker or affinity probe with the composition of Formula (1) after the composition of Formula (I) becomes attached to the active BSH enzyme. The kit may alternatively or in addition contain the composition of Formula (2a) or (2b), which functions as a detectable probe (detectable via $R^5$) for the active BSH enzyme by covalently binding the composition of Formula (2a) or (2b) to the active BSH enzyme via $R^3$, wherein the kit may also include instructions for attaching the composition of Formula (2a) or (2b) to the active BSH enzyme.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A: Scheme of overall chemical strategy to covalently label active BSH enzymes via their active site cysteine. FIG. 1B: Structure of the activity-based probe Ch-AOMK used to identify BSH activity in the gut microbiome. FIG. 1C: Cu-catalyzed azide-alkyne cycloaddition (CuAAC) click chemistry reaction to tag labeled enzymes with an affinity handle or contrast agent (e.g., TAG) for pull-down or imaging of BSH activity. FIG. 1D: Scheme showing how BSH carries out the deconjugation reaction of glyco- and tauro-conjugated bile acids, which is the first major step of bile acid metabolism in the intestines. FIG. 1E: Schematic diagram of identifying BSH activity by (a) fluorescence-based in gel activity assay and (b) mass spectrometry (MS)-based proteomic analysis, following click chemistry.

FIGS. 2A-2B. Ch-AOMK probe labels *Clostridium perfringens* BSH in vitro in a time- and dose-dependent manner. Active or heat-killed (HK) BSH was treated with Ch-AOMK for various amounts of time using Ch-AOMK at 500 µM (FIG. 2A) or varying concentrations of Ch-AOMK at 37° C. for 24 hours (FIG. 2B), after which the samples were tagged using the copper-catalyzed azide-alkyne cycloaddition (CuAAC) with Fluor 488-alkene. The samples were analyzed by SDS-PAGE and visualized by in-gel fluorescence. A.U.=arbitrary unit (top panels of FIGS. 2A and 2B). The bands were quantified by densitometry using Image) (bottom panels of FIGS. 2A and 2B). Error bars represent standard deviation from the mean. * $p<0.05$,  $p<0.01$, * $p<0.001$, n.s.=not significant, (a) n=8 (b) n=6.

FIG. 5A: Bacterial lysates (100 µg) isolated from healthy mouse gut microbiomes were incubated with Ch-AOMK (100 µM) at 37° C. for 24 h. After CuAAC tagging with Fluor 488-alkyne, samples were analyzed by SDS-PAGE, followed by visualization using fluorescence. As a negative control for cysteine iodoacetamide (IA, 20 mM) was added prior to Ch-AOMK. Coomassie staining served as the loading control. FIG. 5B: lysates (2.5 mg) were incubated with Ch-AOMK (100 µM) at 37° C. for 12 h. After CuAAC tagging with biotin-alkyne, labeled proteins were enriched by streptavidin-agarose pull-down and analyzed either by Western blot with streptavidin-HRP or by silver staining. Input is 2% of the elution. FIGS. 5C-5E, 5G, and 5H: Mice were treated with dextran sodium sulfate (DSS, 3% w/v, ad libitum) for 8 d, and (FIG. 5C-5D) bacterial populations from the gut microbiome were lysed and analyzed as in FIGS. 5A and 5B. Arrowhead indicates expected mass of BSHs (35 kDa). The bands were quantified by densitometry using ImageJ (a-d, bottom panels). A.U.=arbitrary unit. FIG. 5E: Phylogenetic tree of BSHs identified within the mouse metagenomic assemblies. Bootstrap confidence levels reflect 100 phylogenetic tree reconstructions and are indicated by the blue circles. Green indicates Firmicutes, magenta indicates Bacteroidetes, and bold indicates active BSHs identified by chemoproteomics using Ch-AOMK labeling, followed by CuAAC-based tagging, enrichment, and protein identification by mass spectrometry (MS)-based proteomics, using a 2-fold enrichment cut-off. Heatmap corresponds to samples from three independent experiments (1-3) from mice treated with DSS, which were also analyzed by MS-based proteomics to identify changes in BSH activity during disease. Red indicates higher BSH activity in DSS compared to control mice, blue indicates lower BSH activity in DSS compared to control mice (Fold change according to heatmap), and gray indicates that the BSH was not identified in the indicated mass spectrometry experiment. FIG. 5F: Fold change (log 2) of enrichment of BSH from healthy mouse microbiomes comparing Ch-AOMK treatment to no Ch-AOMK treatment (y-axis) versus bsh gene abundance using reads per kilobase million (RPKM) in the mice (x-axis). FIG. 5G: Fold change (log 2) of enrichment of BSH from microbioines of mice treated with DSS compared to vehicle controls (y-axis) versus ratio of bsh gene abundance (RPKM) in mice treated with DSS compared to controls (x-axis). The data in FIG. 5G correspond to experiment 2 in FIG. 5E. FIG. 5H: Quantification by MS-based metabolomics of fecal bile acid levels in DSS colitis versus control mice. CA, cholic acid; TCA, taurocholic acid; DCA, deoxycholic acid; TDCA, taurodeoxycholic acid; CDCA, chenodeoxycholic acid; TCDCA, taurochenodeoxycholic acid; LCA, lithocholic acid; MCA, taurolithocholic acid. Each plot indicates the ratio of a corresponding unconjugated to conjugated BA pair. Error bars represent standard deviation from the mean. Interquartile ranges (IQRs, boxes), median values (line within box), whiskers (lowest and highest values within 1.5 times IQR from the first and third quartiles), and outliers beyond whiskers (dots) are indicated. * $p<0.05$,  $p<0.01$, * $p<0.001$, n.s.=not significant, n=(a) 5, (b) 6, (c) 6, (d) 5, (e) 3, (h) 20.

FIG. 6A: Active or heat-killed CGH was treated with 500 µM of Ch-AOMK for various amounts of time as indicated at 37° C., followed by CuAAC with Fluor 488-alkyne. The samples were purified by SDS-PAGE and visualized by fluorescence (excitation wavelength=488 nm). The gel was stained with Coomassie brilliant blue as loading control. Arrow indicates CGH at 37 kDa. FIG. 6B: Biochemical assay was performed to determine activity of CGH over 24 h, using sodium glycocholate as the substrate and glycine formation as the readout. FIG. 6C: Ch-AOMK labels active CGH from *C. perfringens* (10 µg) in a dose-dependent manner. The samples were purified by SDS-PAGE and visualized by fluorescence (excitation wavelength=488 nm). The gel was stained with Coomassie brilliant blue as loading control. Arrow indicates CGH at 37 kDa. N.D.=not detectable, n.s.=not significant, n=3.

FIG. 10A: Bacterial lysate (100 µg) isolated from the mouse gut microbiome was incubated with Ch-AOMK (100 µM) 37° C. for 24 h. Following click chemistry with Fluor 488-alkyne, samples were analyzed by SDS-PAGE, followed by visualization using fluorescence. As a negative control for cysteine labeling, iodoacetamide (IA, 20 mM) was added prior to Ch-AOMK. Coomassie staining served as a loading control. Alternatively, FIG. 10B: lysates (2.5 mg) were incubated with 100 µM of Ch-AOMK at 37° C. for 12 h. After click reaction with biotin-alkyne, samples were pulled down and analyzed by Western blot with streptavidin-HRP or silver staining. Arrow indicates BSH at 35 kDa.

FIG. 12A: Percent weight change was calculated over the course of the DSS treatment. FIG. 12B: Biochemical assay was performed to determine CGH activity during DSS treatment, using sodium glycocholate as the substrate and glycine formation as the readout. FIG. 12C: Bacteria were isolated from fecal samples, and lysates (100 µg) were incubated with Ch-AOMK (100 µM) at 37° C. for 24 h. After CuAAC tagging with Fluor 488-alkyne, samples were analyzed by SDS-PAGE, followed by visualization using fluorescence. Coomassie staining served as the loading control. Alternatively, FIG. 12D: lysates from days 4-8 (2.5 mg) was incubated with Ch-AOMK (100 µM) at 37° C. for 12 h. After CuAAC tagging with biotin-alkyne, samples were enriched using streptavidin-agarose and analyzed either by Western blot with streptavidin-HRP or by silver staining. Arrowhead indicates expected size of BSH (35 kDa). FIGS. 12E-12G: Bacterial composition was taxonomically classified at the phylum (FIG. 12E), class (FIG. 12F), and order levels (FIG. 12G). * $p<0.05$,  $p<0.01$, * $p<0.001$.

FIGS. 13A and 13B. Results of labeling with DCA-AOMK (Compound 4A) and CDCA-AOMK (Compound 4B). DCA-AOMK and CDCA-AOMK label *Clostridium perfringens* bile salt hydrolase (BSH). BSH was labeled with varying concentrations (0-500 µM) of DCA-AOMK (FIG. 13A) or CDCA-AOMK (FIG. 13B) at 37° C. for 24 h, after which the samples were tagged using the copper-catalyzed azide-alkyne cycloaddition (CuAAC) with Fluor 488-alkyne. The samples were analyzed by SDS-PAGE and visualized by in-gel fluorescence. A.U.=arbitrary unit. The bands were quantified by densitometry using imageJ (bottom panels). Error bars represent standard deviation from the mean. * $p<0.05$,  $p<0.01$, *$p<0.001$, n.s.=not significant, n=(A) 3, (B) 5.

DETAILED DESCRIPTION OF THE INVENTION

Figures 1A, 1B, 1C, 1D:
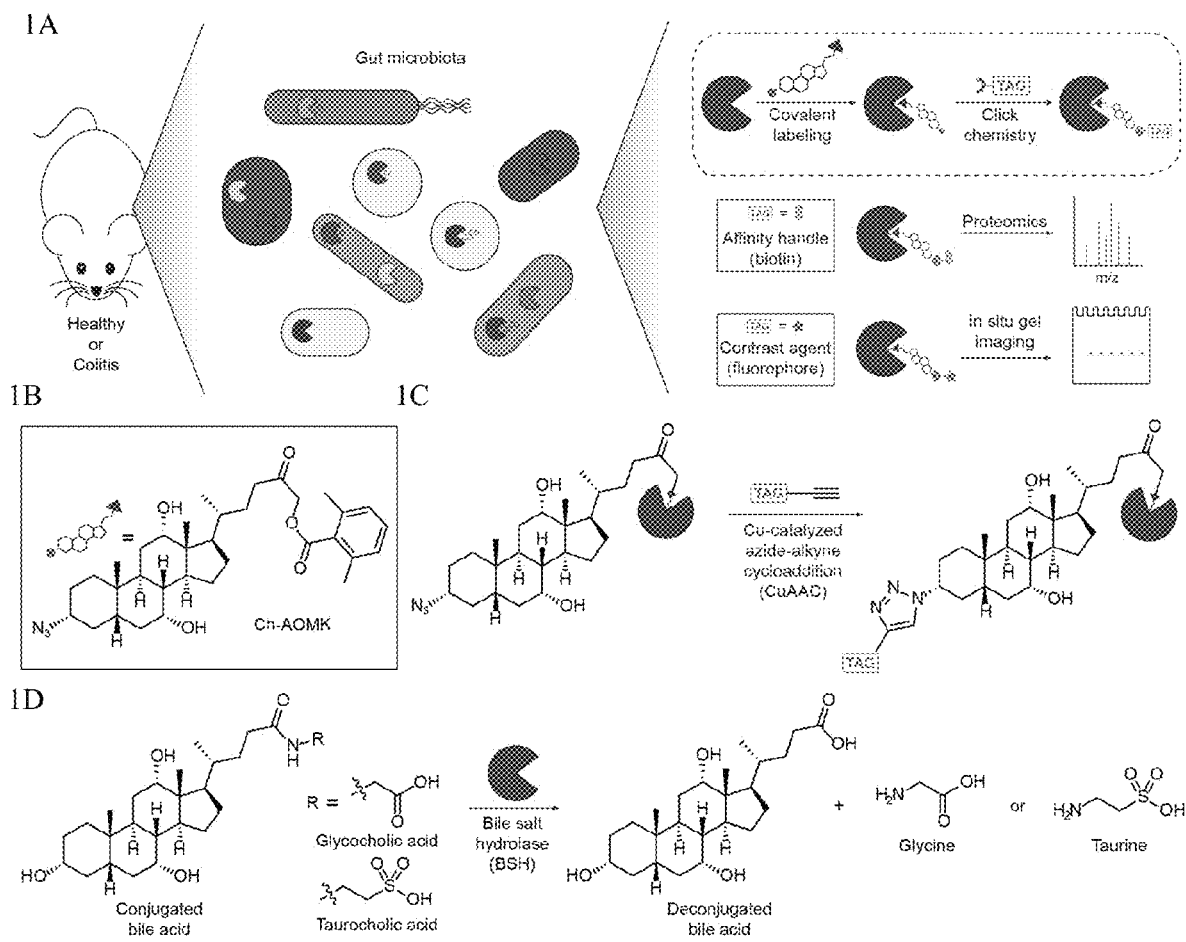
FIGS. 1A-1E. Chemoproteomic, activity-based approach for profiling bile salt hydrolase (BSH) activity within the gut microbiome during health and disease (e.g., colitis).

In one aspect, the present disclosure is directed to cholic acid-based BSH enzyme probe compositions ("probes") having the following structure:

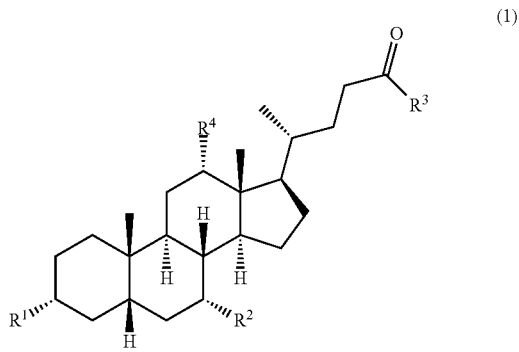
(1)

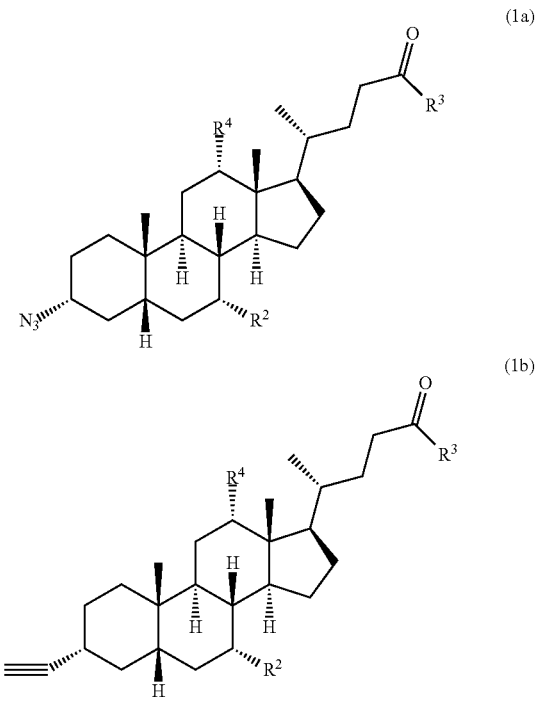

(1a)

(1b)

In the above structure, $R^1$ is independently selected from OH, ester groups, ether groups, amine groups, thiol, thioether groups, halides, and groups containing an alkynyl or azido ($N_3$) functionality. Notably, the alkynyl or azido group can be subsequently used in alkyne-azide click chemistry to attach a tagging molecule to the probe after attachment of the probe (via $R^3$) to the BSH enzyme (wherein the tagging molecule contains a tag and a counterpart click chemistry group to react with and attach to the probe). Thus, for purposes of the present invention, the presence of at least one alkynyl or azido group in Formula (1) is needed. In Formula (1), the ester group may be, for example, an acetate (—OC(O)CH$_3$) or propionate group. The ether group may be, for example, a methoxy, ethoxy, or methoxymethyl group. The amine group may be for example, NH$_2$, NH(CH$_3$), or N(CH$_3$)$_2$. The thiol group refers to —SH. The thioether group may be, for example, —SCH$_3$. The halide may be fluoro, chloro, bromo, or iodo. The groups $R^2$ and $R^4$ may be independently selected from H and any one or more groups described above for $R^1$. The group $R^3$ is a group containing a reactive functionality capable of covalent binding to a thiol or amine. Some examples of groups capable of covalent binding to a thiol include maleimide, acyloxymethylketone, haloacetyl, halomethyl, alkenyl, pyridyl disulfide, and vinylsulfone. Some examples of groups capable of covalent binding to an amine group include succinimide esters, imidoesters, anhydrides, aldehydes, epoxides, acyl azides, and isocyanates. At least one of $R^1$, $R^2$ and $R^4$ is a group containing an alkynyl or azido functionality. In some embodiments, only $R^1$ is or contains an alkynyl or azido functionality. Regardless of the selection of $R^1$, in some embodiments, $R^2$ and $R^4$ are both OH, or $R^2$ and $R^4$ are both H, or one of $R^2$ and $R^4$ is OH while the other is H.

In more particular embodiments, $R^3$ is selected from the group consisting of:

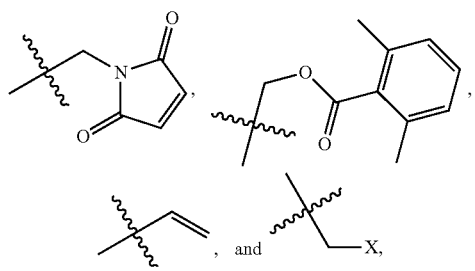

wherein X is a halogen atom.

In more particular embodiments, the probe has any of the following compositions:

In some embodiments of Formulas (1a) and (1b), $R^2$ and $R^4$ are independently selected from H and OH. In one embodiment, both of $R^2$ and $R^4$ are OH. In another embodiment, both of $R^2$ and $R^4$ are H. In another embodiment, one of $R^2$ and $R^4$ is OH while the other is H.

In another aspect, the present disclosure is directed to a method for profiling changes in gut microbiome-associated BSH activity in an organism. In the method, a biological sample containing BSH enzyme is first obtained (step i). The biological sample is generally a gut microbiome sample, which is typically a fecal sample. The sample containing BSH enzyme will generally contain active and inactive BSH enzymes. The method is suitable for any organism that has bile. The organism is typically a vertebrate, or more particularly, a mammal, bird, reptile, amphibian, or fish (e.g., zebrafish, a common model in biology). The mammal is typically human, although the method can be used on other mammals, such as common pets (dogs and cats) or farm animals (e.g., cows and horses).

Subsequently, in step (ii), active BSH enzyme in the biological sample is attached to the BSH activity-based probe ("probe") of Formula (1), via $R^3$ of the BSEI activity-based probe, to provide a probe-BSH enzyme conjugate. Notably, the BSH activity-based probe of Formula (1) provides the significant advantage of being able to selectively attach to active forms of the BSH enzymes. The BSH activity-based probe is able to achieve this selective ability by having a cholic acid base structure, which functions as a substrate of active BSH enzymes. The selective probing of active BSH enzyme is critical for profiling the activity of the BSH enzyme, which in turn can be used to identify markers of certain metabolic disorders, such as IBD, colitis, Crohn's Disease, metabolic syndrome, and obesity. Such profiling may also be used as a diagnostic test for one or more non-metabolic diseases (e.g., cancer or microbial infection). Once the BSH activity-based probe has attached to the active BSH enzyme through $R^3$, the probe bears an alkynyl or azido functionality on any one of $R^1$, $R^2$, or $R^4$, more typically at $R^1$. In the probe-BSH conjugate, the available alkynyl or azido functionality on the probe can undergo a click chemistry reaction with an azide- or alkyne-containing tagging molecule, respectively.

The probe-BSH enzyme conjugate has the following generic structure (after the probe has attached to the BSH enzyme via $R^3$):

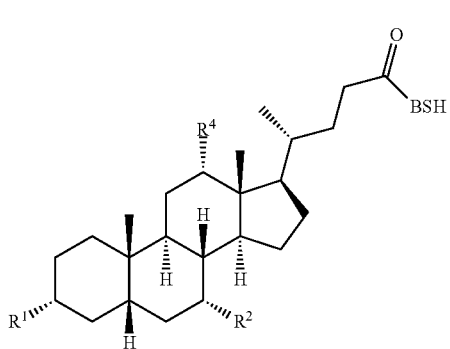

(1-1)

wherein $R^1$, $R^2$, and $R^4$ are as defined in Formula (1) above, and wherein at least one of $R^1$, $R^2$ and $R^4$ is a group containing an alkynyl or azido functionality.

In some embodiments, only $R^1$ is or contains an alkynyl or azido functionality, such as shown in the probe compositions of Formula (1a) and (1b). The respective probe-BSH enzyme conjugates resulting from probe compositions of Formulas (1a) and (1b) are shown as follows:

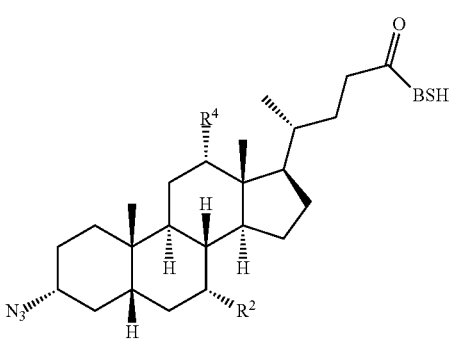

(1-2)

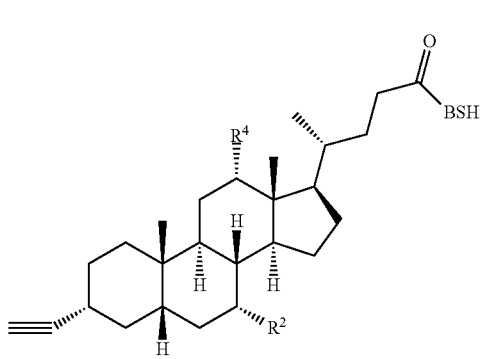

(1-3)

Regardless of the selection of $R^1$ in Formulas (1-1), (1-2), and (1-3), in some embodiments, $R^2$ and $R^4$ are both OH, or $R^2$ and $R^4$ are both H, or one of $R^2$ and $R^4$ is OH while the other is H. The BSI enzyme is attached to the probe by a direct or indirect covalent bond. An indirect covalent bond is a covalent bond containing a linker. Thus, although Formula (1-1) depicts a single covalent bond between the carbonyl carbon of the probe and the BSH, a linker with multiple linking bonds can be included in the shown bond.

In step (iii), after the probe has attached to active BSH enzymes, a tagging molecule containing a tag and either an alkynyl or azido group is reactively attached, via click chemistry, to the probe on the probe-BSH enzyme conjugate to form a tag-BSH enzyme conjugate. More specifically, the alkynyl or azido group of the probe, as attached to the active BSH enzyme, undergoes a click chemistry reaction with an azido or alkynyl group, respectively, present in the tagging molecule.

Aside from containing an azido or alkynyl group, the tagging molecule contains a tag that permits detection. In one embodiment, the tag is directly detectable, such as an organic or inorganic fluorophore or radioactive atom. The directly detectable tag in the tag-BSH enzyme conjugate can be detected and analyzed to obtain a BSH enzyme activity profile (step iv) by, for example, gel electrophoresis or in-gel fluorescence. In another embodiment, the tag is not directly detectable but permits subsequent detection. For example, the tag may be an affinity molecule (i.e., molecule that can engage in an affinity bond, such as a biotin-avidin or biotin-streptavidin bond). In the case of the tagging molecule containing an affinity tag (e.g., biotin, avidin, or streptavidin), the tagging molecule also contains an alkynyl or azido group, as appropriate, for reacting by click chemistry with an azido or alkynyl group, respectively, on the probe attached to the active BSH enzyme. The affinity-tagged BSH enzyme can then be subjected to an enrichment step in which active BSH enzyme obtained from the sample is enriched. Specifically, the affinity-tagged BSH enzyme can be subjected to a pull-down process, as well known in the art, by selective attachment of affinity-tagged BSH enzyme to a stationary material containing a counterpart affinity tag, while non-tagged BSH enzyme (inactive enzyme) is separated from the tagged BSH enzyme. The affinity-tagged BSH enzyme is then released from the stationary material by well-known methods, and can then be detected and analyzed to obtain a BSH enzyme activity profile (step iv) by well known protein characterization techniques, e.g., proteomic methods and/or mass spectroscopy, as well known in the art.

The tag-BSH enzyme conjugate has the following generic structure:

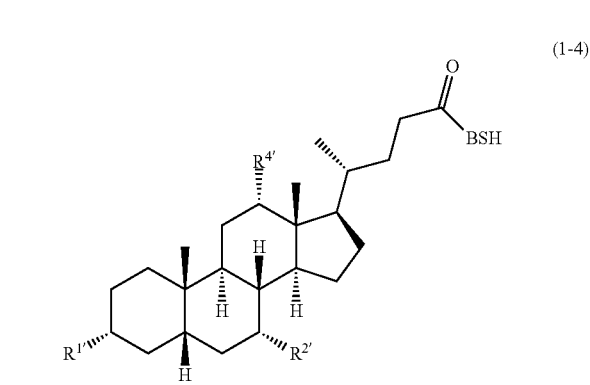

(1-4)

wherein R$^{1'}$ is OH, ester group, ether group, amine, thiol, thioether, halide, or a group R$^a$; R$^{2'}$ is H, OH, ester group, ether group, amine, thiol, thioether, halide, or a group R$^a$; R$^{4'}$ is H, OH ester group, ether group, amine, thiol, thioether, halide, or a group R$^a$; wherein one of R$^{1'}$, R$^{2'}$ and R$^{4'}$ is R$^a$, wherein R$^a$ is

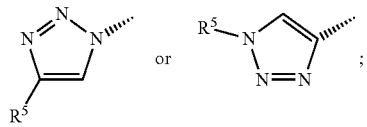

wherein R$^5$ is a tag, as described above, useful for detecting the BSH enzyme. Regardless of the selection of R$^1$, in some embodiments, R$^2$ and R$^4$ are both OH, or R$^2$ and R$^4$ are both H, or one of R$^2$ and R$^4$ is OH while the other is H.

In specific embodiments, the tag-BSH enzyme conjugate produced in step (iii) has any of the following structures:

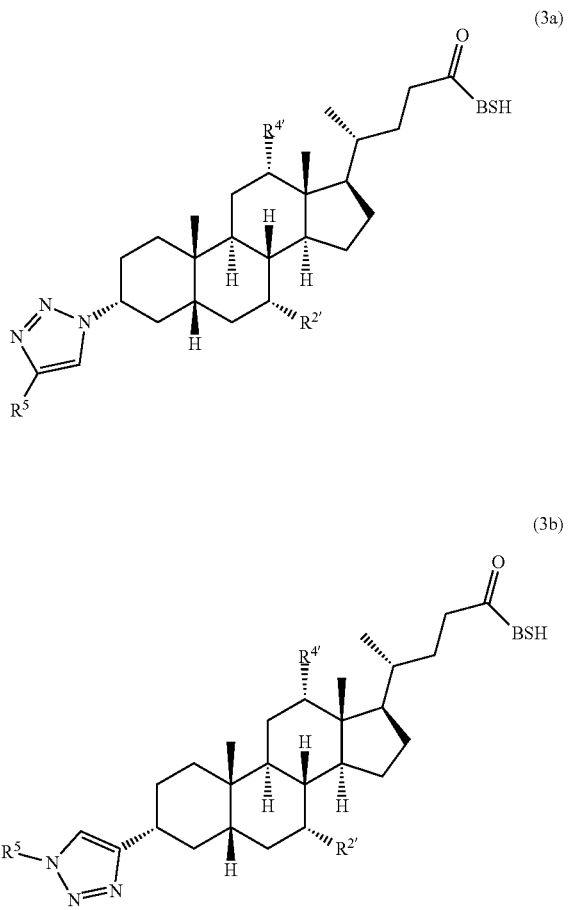

In Formulas (3a) and (3b), R$^{2'}$ is H, OH, ester group, ether group, amine, thiol, thioether, or halide; R$^{4'}$ is H, OH, ester group, ether group, amine, thiol, thioether, or halide; R$^5$ is a tag (as described above) that permits detection of the BSH enzyme. In one embodiment, the tag is a directly detectable label, such as a fluorophore, metal nanoparticle, or radionuclide. In another embodiment, the tag is an affinity tag, wherein the affinity tag is a molecule capable of forming an affinity bond with another molecule. The affinity tag may be, for example, biotin, avidin, streptavidin, antigen, or an antibody.

In some embodiments, the detecting step (iv) quantifies the amount of labeling to provide a total BSH enzyme activity. In other embodiments, the detecting step (iv) further includes identifying the active BSH enzymes that were labeled. The BSH enzymes can be identified by any of the protein characterization methods known in the art, including gel electrophoresis, fluorescence, and mass spectroscopy. In some embodiments, a change (increase or decrease) in the amount of labeled BSH enzymes compared to a control indicates a disorder, such as colitis, metabolic syndrome, obesity, cancer, or infection. The colitis may be, for example, inflammatory bowel disease, ulcerative colitis, or Crohn's disease.

The present disclosure is also directed to a kit for labeling an active BSH enzyme with a probe and making the probe detectable. The kit typically includes: i) the composition of Formula (1), which functions as a probe for the active BSH enzyme by covalently binding the composition of Formula (1) to active BSH enzyme in the sample via R$^3$ to form a probe-BSH enzyme conjugate, and ii) a molecule that contains a tag (e.g., detectable marker or affinity probe), wherein the tagging molecule forms a covalent bond with the probe portion of the probe-BSH enzyme conjugate to form a tag-BSH enzyme conjugate. The kit may also further include: iii) instructions for obtaining and/or preparing a sample containing the BSH enzyme, instructions for attaching the probe composition of Formula (1) to the active BSH enzyme in the sample to form the probe-BSH enzyme conjugate, and instructions for attaching the tag molecule to the probe-BSH enzyme conjugate to form the tag-BSH enzyme conjugate. The kit may further include instructions for removing excess (free) probe and tag molecules. The kit may alternatively or in addition contain the composition of Formula (2a) or (2b), which functions as a detectable probe (detectable via R$^5$) for the active BSH enzyme by covalently binding the composition of Formula (2a) or (2b) to the active BSH enzyme via R$^3$, wherein the kit may also include instructions for attaching the composition of Formula (2a) or (2b) to the active BSH enzyme.

Examples have been set forth below for the purpose of illustration and to describe the best mode of the invention at the present time. However, the scope of this invention is not to be in any way limited by the examples set forth herein.

EXAMPLES

Overview

Chemoproteomic tools such as activity-based probes (ABPs) have the unique capacity to target desired enzymatic activities within complex biological systems and have thus revolutionized the ability to discover and characterize enzymes without the need for purification or heterologous expression of the target enzymes. ABPs comprise a targeting group to direct the probe to enzymes of interest and a selective, electrophilic chemical warhead to covalently label an active site nucleophilic residue, once the enzyme has bound the targeting group. The enzymatic activity can be detected by inclusion within the ABP of a bioorthogonal handle that can subsequently undergo a click chemistry tagging reaction, such as the copper-catalyzed azide-alkyne cycloaddition (CuAAC), to endow the target protein with an imaging agent or affinity probe. ABPs have been applied to detect enzymatic activity from complex biological samples by either visualization using imaging modalities or protein identification by pull-down using affinity-based reagents, followed by mass spectrometry (MS)-based proteomics.

The following experiments demonstrate a convenient method for detecting and identifying changes in BSH enzymatic activity that could be used for assessing alterations to global BA metabolism in mouse models of IBD. To achieve this, a trifunctional ABP was designed and synthesized to profile BSH activity within the gut microbiome in healthy and colitis samples.

Synthesis of Ch-AOMK BSH Activity Probe

The following synthetic scheme was used:

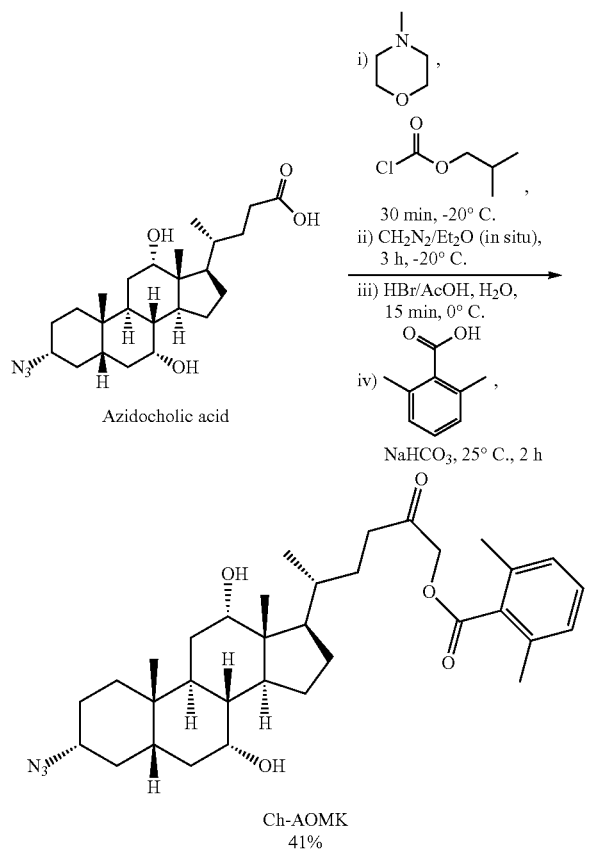

Azidocholic acid (300 mg, 0.7 mmol) was dissolved in anhydrous THF (3.64 mL) and stirred in a dry ice/acetone bath at −15° C. for 5 min. N-methylmorpholine (98.1 μL, 0.866 mmol, 1.25 eq.) and isobutyl chloroformate (104 μL, 0.8 mmol, 1.15 eq.) were sequentially added to this solution, and the mixture was stirred at −15° C. for an additional 30 minutes, during which a white precipitate formed. The reaction was brought to 0° C. Ethereal diazomethane was generated in situ according to the procedure reported in the Sigma Aldrich technical bulletin (AL-180). A flame polished glass pipette was used to add diazomethane (3 mmol, 3.75 eq.) dropwise to the reaction mixture at 0° C., and the reaction was slowly warmed to room temperature over 4 hours. To generate the corresponding bromomethyl ketone, the reaction mixture was cooled to 0° C. Hydrogen bromide (33 w % in acetic acid, 5 mL, 75 mmol, 107 eq.) was mixed with 10 mL of water and added to the reaction mixture, dropwise until the evolution of nitrogen gas stopped. The mixture was diluted with ethyl acetate and transferred to a separatory funnel. The organic layer was washed sequentially with water, brine, and $NaHCO_3$, then dried over anhydrous $Na_2SO_4$. The organic layers were combined and rotovapped to yield a sticky yellow solid.

The crude was dissolved in dry DMF (0.7 mL) and was stirred at room temperature under nitrogen, and 2,6-dimethylbenzoic acid (30 mg, 0.2 mmol, 0.28 eq.) and sodium bicarbonate (17 mg, 0.2 mmol, 0.28 eq.) were added. After 2 hours, the reaction mixture was diluted with ethyl acetate and transferred to a separatory funnel. The organic layer was washed with water three times and dried over anhydrous $Na_2SO_4$. The crude was purified by flash column chromatography (2% MeOH in DCM) to yield a sticky solid. The solid was dissolved in DMSO and further purified by HPLC to generate the purified compound as a white powder (41% yield). TLC ($CH_2Cl_2$:MeOH, 99:1 v/v): $R_f$=0.6; $^1$H NMR (500 MHz, DMSO-d6): δ 7.27 (t, J=7.5 Hz, 1H), 7.11 (d, J=3.75 Hz, 2H), 5.05 (s, 2H), 4.17 (m, 2H), 3.80 (s, 1H), 3.63 (s, 1H), 3.23 (m, 1H), 2.41 (m, 2H), 2.32 (s, 6H), 2.10 (m, 2H), 1.99 (s, 1H), 1.83 (m, 2H), 1.75 (m, 2H), 1.66 (m, 2H), 1.58 (m, 2H), 1.39 (m, 7H), 1.23 (m, 2H), 1.00 (m, 1H), 0.95 (d, J=2.5 Hz, 4H), 0.85 (s, 3H), 0.6 (s, 3H); $^{13}$C NMR (500 MHz, DMSO-d6): δ 204.58, 177.34, 168.75, 135.19, 133.49, 130.03, 128.01, 71.45, 68.79, 66.57, 61.25, 46,51, 46.24, 41.97, 41.86, 35.51, 35,46, 35.37, 34.97, 34.79, 29.38, 28.92, 27.68, 26.79, 26.60, 23.21, 22.95, 19.77, 17.60, 12.80; ESI-MS (m/z): [M-H]$^-$ calcd. For $C_{34}H_{48}N_3O_5^-$, 578.3599; found, 578.3570. Safety statement: Significant hazards were mitigated in the generation of diazomethane by using ground glass joints, a blast shield, and loosely sealing the reaction vessel. Afterwards, the syringes, needles, and glassware were quenched with acetic acid.

Mice: C57Bl/6 mice were purchased from Jackson Laboratories and bred in house at the animal facility of Cornell University. Mice were used at 10-15 weeks of age in accordance with the guidelines of the Institutional Animal Care and Use Committee and the Cornell Center for Animal Resources and Education (Protocol Number 2015-0069). Mice were co-housed for 7 d prior to use.

Dextran sodium sulfate (DSS) colitis: Mice were treated with DSS (0 or 3% w/v in drinking water, ad libitum) for 8 d. The mice were weighed daily, and fecal samples were collected throughout the treatment. Mouse feces pellets were collected on dry ice, flash frozen, and stored in the −80° C. freezer until further use.

Bacteria cultures: *Bifidobacterium longum* subsp. infantis ATCC15697 and *Bifidobacterium bifidum* DSM20456 strains were purchased from American Type Culture Collection (ATCC). Bifidobacterium species were grown in Bifidobacterium broth supplied by ATCC, anaerobically at 37° C. until the stationary phase, after which they were aliquoted into tubes, pelleted down (4,500×g, 30 min), flash frozen, and stored at −80° C. until further use.

Cloning of *C. perfringens* choloylglycine hydrolase (CGH): CGH from *C. perfringens* strain 13A was amplified from a synthetic gene fragment (gBlocks, Integrated DNA Technologies) and cloned into the pET-21b vector with an ampicillin resistance gene. Briefly, two forward primers containing a NdeI restriction site for constructing wildtype CGH, (WT, CTAGCATATGTGTACCGGATTAGCGCTG-GAG, SEQ ID NO: 1) or a point mutant (cysteine 2 to serine, C2S, CTAGCATATGTCTACCGGATTAGCGCTGGA-GAC, SEQ ID NO: 2) and a shared reverse primer (CTAGCTCGAGCTTATCGTCGT-CATCCTTGTAATCGTTCACGTGGTTGATGCTCAG, SEQ ID NO: 3), which was designed containing an XhoI restriction site and a C-terminal FLAG peptide (DYKDDDDK, SEQ ID NO: 4) epitope tag, were used to amplify WT or C2S CGH.

*C. perfringens* CGH protein expression: The pET-21b expression plasmid (WT or C2S CGH) was introduced into *E. coli* Rosetta 2 (DE3) pLysS competent cells. The resulting colonies were cultured in Terrific Broth liquid medium (12 g/L BactoTryptone, 23.9 g/L yeast extract, 8 ml/L glycerol, 0.22 g/L $KFI_2PO_4$, 0.94 g/L $K_2HPO_4$) in the presence of ampicillin (50 μg/ml) at 37° C. to an OD600 of 0.5-0.6. The expression of CGH was induced by the addition of IPTG (0.1 mM), and the cells were incubated at 18° C. for 18 hours with shaking (220 rpm). The cells were harvested by centrifuging at 12,000×g for 1 min at 4° C. The supernatant was discarded, and the pellet was resuspended in 20 mM sodium phosphate buffer (pH 7.0) containing 1 mM EDTA, 10 mM DTT and 1 mM PMSF, and lysed by sonication. The tube was centrifuged at 16,000×g for 30 min at 4° C., and the supernatant was collected and quantified by the DC assay (Bio-Rad).

General method for methanol-chloroform protein precipitation: To 20 μL of reaction mixture was added 200 μL of methanol, 75 μL of chloroform, 150 μL of water, sequentially. The sample was then vortexed and centrifuged at 13,000×g for 15 min at 4° C. The aqueous layer was removed without disturbing the protein layer. Cold methanol (1 mL) was added, and the tube was inverted a few times gently without disturbing the precipitated protein. The tube was centrifuged at 13,000×g for 10 min at 4° C. and decanted, leaving the pellet intact. The pellet was again washed with 1 mL of cold methanol, centrifuged at 13,000×g for 10 min at 4° C., and the supernatant was decanted. The pellets were left to dry for 3-5 min at 37° C., after which they were resolubilized in the appropriate buffer for each assay.

General method for TCA-acetone protein precipitation: To the reaction mixture (100 μL-2 mL, see Table 1, vide infra) was added TCA at a final concentration of 1.5% (w/v). The samples were chilled on ice for 30 min. The precipitate was pelleted down for 30 min at 4° C. and 20,000×g, and the supernatant was decanted carefully. Cold acetone (−20° C., 1 mL) was added to the pellet, and the sample was sonicated briefly until the pellet was broken up, after which the protein was pelleted down (20,000×g, 4° C., 5 min). The pellet was washed two more times with cold acetone (1 mL), and the supernatant was decanted. The pellets were left to dry for 3-5 min at 37° C. after which they were resolubilized in the appropriate buffer for each assay.

General method for copper-catalyzed azide-alkyne cycloaddition (CuAAC) or click chemistry: The reaction was carried out in click buffer (0.1 M sodium phosphate buffer, 4% SDS, pH 7.4) for a final reaction volume of 20 μL-2 mL, see Table 1 below. Copper-THPTA complex was formed by mixing copper(II) sulfate pentahydrate with THPTA to yield a concentration of 10 and 20 mM, respectively. Then, either Fluor 488-allkyne (10 μM) or biotin-alkyne (50 μM), preformed copper-THPTA complex (final concentration of 1 mM and 2 mM, respectively), and sodium ascorbate (100 μM) were added sequentially. The tubes were gently mixed between the addition of each reagent. The tubes were incubated at 37° C. for 2 h (in the dark for fluorescence-based in-gel activity assay).

TABLE 1

Conditions for Ch-AOMK labeling of bacterial samples, followed by click chemistry.

| Experiment | [Ch-AOMK] μM | Time (h) | Protein amount | Probe reaction vol. | pH | Click reaction vol. | Precipitation method |
|---|---|---|---|---|---|---|---|
| CP FL (time) | 500 | 0-24 | 10 μg | 20 μL | 5.6 | 20 μL | MCA |
| CP FL (dose) | 0-500 | 24 | 10 μg | 20 μL | 5.6 | 20 μL | MCA |
| *E. coli* FL | 500 | 24 | 50-250 μg | 20 μL | 5.6 | 20 μL | MC |
| *E. coli* PD | 500 | 24 | 2.5 mg | 100 μL | 5.6 | 100 μL | MC |
| BB FL | 500 | 24 | 100 μg | 20 μL | 6.3 | 20 μL | MC |
| BL FL | 500 | 24 | 100 μg | 20 μL | 6.3 | 20 μL | MC |
| BB PD | 500 | 24 | 2.5 mg | 200 μL | 6.3 | 100 μL | MC |
| BL PD | 500 | 24 | 2.5 mg | 200 μL | 6.3 | 100 μL | MC |
| BB PD MS | 500 | 24 | 10 mg | 800 μL | 6.3 | 400 μL | MC |
| BL PD MS | 500 | 24 | 10 mg | 800 μL | 6.3 | 400 μL | MC |
| Microbiome FL | 500 | 24 | 100 μg | 20 μL | 5.5 | 20 μL | MC |
| Microbiome PD | 100 | 12 | 2.5 mg | 500 μL | 5.5 | 100 μL | TA |
| Microbiome PD MS | 100 | 12 | 25-50 mg | 5-10 mL | 5.5 | 1-2 mL | TA |

Abbreviations: CP, *C. perfringens*; BB, *B. bifidum*; BL, *B. longum*; FL, fluorescence-based in gel activity assay; PD, biotin-streptavidin pull-down; MS, mass spectrometry-based proteomics; MCA, methanol-chloroform-acetone; MC, methanol-chloroform; TA, TCA-acetone.

13,000×g for 10 min at 4° C., and the supernatant was decanted. The pellets were left to dry for 3-5 min at 37° C., after which they were resolubilized in the appropriate buffer for each assay.

Methanol-chloroform-acetone protein precipitation: To 20 μL of reaction mixture was added 200 μL of methanol, 75 μL of chloroform, 150 μL of water, sequentially. The sample was vortexed and centrifuged at 13,000×g for 15 min at 4° C. The aqueous layer was removed without disturbing the protein layer, after which the organic layer was carefully removed using a gel loading tip. Cold methanol (1 mL) was added, and the tube was inverted a few times gently, leaving the protein layer intact. The tube was centrifuged at 13,000×g for 10 min at 4° C. and decanted, leaving the pellet intact. The pellet was again washed with 1 mL of cold General method for fluorescence-based in-gel activity assay: Ch-AOMK (500 μM) was incubated with 100 μg (unless otherwise noted) bacterial lysate at 37° C. for 24 hours. For the inactivation of global cysteine residues, including the lysate was incubated with 20 mM of iodoacetamide at 37° C. for 2 hours prior to Ch-AOMK addition. Excess Ch-AOMK was removed by methanol-chloroform precipitation as above. The pellet was resuspended in click buffer, and click chemistry was carried out in the presence of Fluor 488-alkyne as above. After CuAAC, excess fluorophore was removed by methanol-chloroform precipitation. The pellet was boiled in 20 μL of 1X SDS loading buffer at 95° C. and mixed periodically for 20 min. The samples were purified using a 12% SDS-PAGE gel. The gel was then incubated in fluorescence destaining, solution (40% methanol, 50% acetic acid, 10% water) on a rocker in the dark for 1 hour. The gel was rinsed with water and imaged at an excitation wavelength of 488 nm using a Bio-Rad ChemiDoc MP Imaging System (fluorescence mode). The gel was subsequently stained with Coomassie brilliant blue for 15 min. For destaining, the gel was incubated in Coomassie destaining solution (30% methanol, 5% acetic acid, 65% water) on a rocker overnight and imaged the following day using a Bio-Rad ChemiDoc MP Imaging System (colorimetric mode).

In vitro labeling of purified CGH from *C. perfringens* with Ch-AOMK: CGH from *C. perfringens* (Sigma Aldrich) was resuspended in sodium phosphate buffer (10 mM, pH 7.0) to a final concentration of 10 mg/mL. Unless otherwise mentioned, 10 μg of CGH was incubated in reaction buffer (50 mM sodium acetate, pH 5.6) in the presence of various concentrations of Ch-AOMK (0-500 μM) for various amounts of time (0-24 h) at 37° C. For the heat-killed samples, 10 μg of CGH was incubated in reaction buffer (20 μL) and incubated at 80° C. for 20 min to deactivate the enzyme before Ch-AOMK addition. Prior to the fluorescence-based in-gel activity assay, the reaction mixture was doped with 200 μg of BSA for efficient precipitation of proteins using methanol-chloroform-acetone precipitation as above to remove excess Ch-AOMK (or click chemistry reagents. BSA was visualized with Coomassie staining, which served as a loading control for the samples.

General method for lysing *E. coli, B. bifidum*, and *B. longum*: Bacterial pellets were resuspended in 20 mM sodium phosphate buffer (pH 7.0) containing 1 mM EDTA, 10 mM DTT, and 1 mM PMSF (250 μL of buffer for each 50 mL culture). The samples were then transferred to a 2 mL screwcap tube (for each 50 mL culture). Zirconia/silica beads (330 mg) were added to the tube, which was then subjected to agitation on a bead beater (8 cycles of 1 min beating, followed by 3 min on ice). The samples were centrifuged at 16,000×g to remove the beads and cell debris. The supernatant was transferred to a 1.5 mL microfuge tube, and the concentration was measured by the DC assay.

Isolation of bacteria from mouse gut microbiome and lysis: The following bacterial isolation procedure was carried out on ice where possible. Pellets were thawed and crushed in 1X PBS in an autoclaved mortar and pestle (70 mL of 1X PBS per 15 g wet weight of feces), and the mixture was centrifuged at 300×g for 5 min at 4° C. The supernatant was transferred to another 50 mL conical tube, and the centrifugation was repeated two more times to remove fecal matter. Then, the clarified supernatant was transferred to a clean vessel. Meanwhile, Nycodenz (500 μL, 50% w/v, autoclaved) was added to 1.5 mL microfuge tubes, and 1 mL of the supernatant was carefully layered on top of the gradient. The biphasic solution was then centrifuged at 10,000×g for 40 min at 4° C. After centrifugation, the top layer was carefully removed, leaving the middle layer of bacteria undisturbed. Then, the bacterial layer was carefully pipetted out and combined in a 50 mL conical tube. The collected bacteria were mixed thoroughly and aliquoted into multiple 1.5 mL microfuge tubes, each with 500 μL of mixture. The bacteria were washed with 1 mL of 1X PBS 3 times by thorough resuspension, followed by centrifugation at 16,000×g for 5 min at 4° C. The final pellet was resuspended in 200 μL of buffer (20 mM sodium phosphate buffer (pH 7.0) containing 1 mM EDTA, 10 mM DTT and 1 mM PMSF), and the samples were transferred to a 2 mL screw cap tube containing 330 mg of 0.1 mm zircona/silica beads. The samples were heated 5 times (each time with 1 min beating, followed by 4 min on ice). The samples were then centrifuged at 16,000×g for 30 min at 4° C., and the supernatant was transferred to a clean tube. The protein concentration was measured using the DC assay.

General method for labeling of bacterial lysates with Ch-AOMK: Unless otherwise mentioned, lysates were incubated with 10× reaction buffer (500 mM sodium acetate buffer at the optimized pH, see Table 1) and a final Ch-AOMK concentration of 0-500 μM (25 mM stock in DMSO) for 12-24 h at 37° C.

General method for enrichment of biotin-labeled proteins following click chemistry: Ch-AOMK (100-500 μM) was incubated with bacterial lysate (2.5-50 mg) at 37° C. for 12-24 hours (see Table 1). Excess Ch-AOMK was removed by the precipitation method indicated in Table 1. The pellet was resuspended in click buffer by sonication, and the click reaction was carried out in the presence of biotin-alkyne as above. After the click reaction, excess biotin-reagent was removed by precipitation as above (Table 1). The dried protein pellet was resuspended in 166 μL of 1.2% SDS (per 2.5 mg of protein lysate) in 1X PBS by sonication, and 834 μL of 1X PBS was added to dilute the final concentration to 0.2% SDS. Lysates (50 μg, 2% of elution) were collected as the input control. In the meantime, 10 μL of streptavidin agarose beads (per 2.5 mg of lysate) were washed three times with 1 mL of 0.2% SDS in PBS. The sample was added to the beads and incubated at room temperature for 1 h on a rotator. The tubes were centrifuged at 13,000×g for 1 min at 4° C., and the supernatant was discarded. The beads were sequentially washed with 1 mL of 1%, 0.5%, 0.2% and 0% SDS in PBS. The beads were then subjected to elution as described below.

General protocol for elution of proteins from streptavidin agarose beads for silver staining and Western blotting: After washing the beads with decreasing concentrations of SDS as above, 30 μL of 2X SDS was added to the beads. The samples were then incubated at 25° C. for 5 min, followed by 95° C. for 30 min. The tubes were centrifuged at 13,000×g for 1 min at room temperature, and the supernatant was transferred to another tube for visualization by silver staining and Western blot analysis.

Silver staining: The elated protein lysates (25 μL) were purified using a 12% SDS-PAGE gel. The gel was fixed in fixation buffer (50% methanol, 5% acetic acid, 45%) water) for 20 min. The gel was then washed with 50% methanol, followed by water, for 10 min each. The gel was sensitized by incubating it in 0.02% (w/v) sodium thiosulfate for 1 min, after which it was rinsed with water 5 times. The gel was incubated with 0.1% (w/v) silver nitrate with 0.08% paraformaldehyde for 20 min and rinsed with water 6-7 times to remove excess silver. The gel was developed by incubating it in 50 mL of 2% (w/v) sodium carbonate with 0.04% paraformaldehyde with mild agitation until bands began to appear. After the desired level of signal to noise was obtained, 1 mL of acetic acid was added to quench the development. The gel was rinsed with water 6-7 times and imaged using a Bio-Rad ChemiDoc MP Imaging System (colorimetric mode).

Western blot: Briefly, 5 μL of the eluted protein lysates was purified using a 12% SDS-PAGE gel. After transfer of proteins to a nitrocellulose membrane, the blot was incubated in blocking solution (5% BSA in Tris buffer (500 mM, pH 7.6) with 0.5% Tween-20 (TBST)) for 1 hour, after which the membrane was incubated with streptavidin-HRP (in 5% BSA in TBST) for 1 hour. The blot was rinsed three times with TBST for 10 min, developed with Clarity Western ECL Blotting Substrates (Bio-Rad), and imaged using a Bio-Rad ChemiDoc MP Imaging System (chemiluminescence mode).

Bile salt hydrolase activity assay: BSH activity assay was performed according to the conventional procedure but with the following modifications. Briefly, 12.5 μL each of 20 mM sodium phosphate buffer (pH 5.6), 18 mM sodium glycocholate, 107 mM β-mercaptoethanol, and 55 mM EDTA were mixed, and 45 μL of the reaction mixture was transferred to a separate 1.5 mL microfuge tube. Purified CGH was diluted with 20 mM sodium phosphate buffer (pH 5.6) to obtain a final concentration of 3 Units/μL, 5 μL of which was added to the reaction tube, and the samples were incubated at 37° C. After 1 hour, 50 μL of TCA was added to quench the reaction, and 20 μL of the final mixture was transferred to another tube. Equal volumes of 4% (w/v) ninhydrin in 2-methoxyethanol and 0.16% (w/v) stannous chloride in 200 mM sodium citrate buffer (pH 5.0) were mixed to generate the development solution. This solution (200 μL) was subsequently added to the tube containing 20 μL of the reaction mixture, and the samples were boiled at 95° C. for 20 min. The mixture was diluted 10-fold, and 200 μL was transferred to a 96-well plate for UV absorbance readings at 600 nm. A standard curve using glycine at various concentrations was simultaneously developed and analyzed.

ORBITRAP FUSION™ by FT-Q-IT mode for on-bead or gel-based protein IDs and associated label-free quantitation (LFQ): General protocol for in-gel digestion for identification of proteins: After washing the beads with decreasing concentrations of SDS in PBS as above, 120 μL of 2X SDS was added to the beads. The samples were incubated at 25° C. for 5 min, followed by 95° C. for 30 min. The tubes were centrifuged at 13,000×g for 1 min at room temperature, and the supernatant was transferred to another 1.5 mL microfuge tube. The eluted protein lysates (110 μL) were purified with a 12% SDS-PAGE gel using both a pre-stained and unstained protein ladder for gel excision. The gel was fixed in the fixation buffer (50% methanol, 10% acetic acid, 40% water) overnight and transferred to gel storage buffer (10% methanol, 7% acetic acid, 83% water) before excision.

The proteins in the gel were visualized with SYPRO™ Ruby Protein Gel Stain (Thermo Fisher Scientific), and the desired bands were cut into ~1 mm cubes and subjected to in-gel digestion, followed by extraction of the tryptic peptide as reported previously (Yang, Y., et al., Electrophoresis 2007, 28 (12), 2080-2084). The excised gel pieces were washed consecutively in 200 μL water, 100 mM ammonium bicarbonate/acetonitrile (1:1), and acetonitrile. The gel pieces were reduced with 250 μL of 10 mM DTT in 100 mM ammonium bicarbonate for 1 h at 56° C. and alkylated with 260 μL of 55 mM iodoacetamide in 100 mM ammonium bicarbonate at room temperature in the dark for 1 hour. After wash steps as described above, the gel slices were dried and rehydrated with 10 μL trypsin in 50 mM ammonium bicarbonate, 10% acetonitrile (10 ng/μL) at 37° C. for 16 hours. The digested peptides were extracted twice with 20 μL of 50% acetonitrile, 5% formic acid and once with 20 μL of 90% acetonitrile, 5% formic acid. Extracts from each sample were combined. Due to the large gel volume of the samples, the extracted peptide solution was filtered with a COSTAR® 0.22 μm spin filter (Corning #8161) and then lyophilized.

On-bead digestion for identification of proteins: After washing the beads with decreasing concentrations of SDS in PBS as above, the beads were incubated with 500 μL of 6M urea (in PBS) with 10 mM TCEP at 37° C. for 30 min, and then 25 μL of 400 mM iodoacetamide was added. The samples were then incubated at 37° C. for 30 min. In the meantime, trypsin was activated by incubating at 30° C. for 15 min. The beads were washed with 1 mL of 1M urea in PBS, after which the samples were incubated with 2 μg trypsin (in 200 μL of 1M urea with 1 mM CaCl₂ in PBS, pH 8.0) at 37° C. overnight with gentle rotating. The supernatant was removed, and 800 μL of water was added to bring the final volume to 1 mL. The samples were acidified with 1N HCl (6 μL) to reach a pH of ~2.6 to inactivate trypsin and then lyophilized.

Protein identification by nano LC/MS/MS analysis: The tryptic digests were reconstituted in 20 μL of 0.5% formic acid for nanoLC-ESI-MS/MS analysis, which was carried out using an ORBITRAP FUSION™ TRIBRID™ (Thermo Fisher Scientific, San Jose, CA) mass spectrometer equipped with a nanospray FLEX™ Ion Source and coupled with a Dionex ULTIMATE™ 3000 RSLCnano system (Thermo, Sunnyvale, CA). The samples (5-15 μL) were injected onto a PEPMAP™ C-18 RP nano trapping column (5 μm, 100 μm i.d.×20 mm) at a 20 μL/min flow rate for rapid sample loading and then separated on a PEPMAP™ C-18 RP nano column (2 μm, 75 μm×25 cm) at 35° C. The tryptic peptides were eluted in a 120 min gradient of 5% to 38% acetonitrile in 0.1% formic acid at 300 nL/min, followed by a 7 min ramping to 90% acetonitrile, 0.1% formic acid and an 8 min hold at 90% acetonitrile, 0.1% formic acid. The column was re-equilibrated for 25 min prior to the next run. The ORBITRAP FUSION™ was operated in positive ion mode with spray voltage set at 1.6 kV and source temperature at 275° C. External calibration for FT, IT and quadrupole mass analyzers was performed. In data-dependent acquisition (DDA) analysis, the instrument was operated using FT mass analyzer in MS scan to select precursor ions followed by 3 s "Top Speed" data-dependent CID ion trap MS/MS scans at 1.6 m/z quadrupole isolation for precursor peptides with multiple charged ions above a threshold ion count of 10,000 and normalized collision energy of 30%. MS survey scans at a resolving power of 120,000 (fwhm at m/z 200), for the mass range of m/z 375-1575. Dynamic exclusion parameters were set at 40 s of exclusion duration with ±10 ppm exclusion mass width. All data were acquired under XCALIBUR™ 3.0 operation software (Thermo Fisher Scientific).

Proteomics data analysis: The DDA raw files for CID MS/MS were subjected to database searches using Proteome Discoverer (PD) 2.2 software (Thermo Fisher Scientific, Bremen, Germany) with the Sequest HT algorithm. The PD 2.2 processing workflow containing an additional node of Minora Feature Detector for precursor ion-based quantification was used for protein identification and relative quantitation analysis between samples. The database search was conducted against the appropriate bacterial strain(s), available publicly on NCBI or UniProt or the metagenomic assemblies, plus a common contaminant (246 entries) database. Two-missed trypsin cleavage sites were allowed. The peptide precursor tolerance was set to 10 ppm, and fragment ion tolerance was set to 0.6 Da. Variable modification of methionine oxidation, deamidation of asparagine/glutamine and fixed modification of cysteine carbamidomethylation, were set for the database search. Only high confidence peptides defined by Sequest HT with a 1% FDR by Percolator were considered for the peptide identification. The final protein IDs contained protein groups that were filtered with at least two peptides per protein and one unique peptide.

Relative quantitation of identified proteins between samples was determined by the Label Free Quantitation (LFQ) workflow in PD 2.2. The precursor abundance intensity for each peptide identified by MS/MS in each sample were automatically determined, and the unique peptides for each protein in each sample were summed and used for calculating the protein abundance by PD 2.2 software without normalization. Protein ratios were calculated based on pairwise ratios for each sample. The proteins that were considered enriched were cut-off using a ≥2-fold ratio of with probe compared to no probe in the healthy mouse gut microbiome samples.

DNA isolation and shotgun metagenomic library preparation: Fecal DNA was prepared from 3-4 frozen pellets collected from mice treated with or without DSS using the Quick-DNA™ Fecal/Soil Microbe Miniprep Kit (Zymo Research, Catalog No. D6010) according to the manufacturer's instructions with minor modifications. Instead of vortexing, the samples were placed in a RETSCH™ 96 Well Plate Shaker (MO BIO Catalog #11996) for 10 min. The concentration of isolated DNA was assessed using QUBIT™ dsDNA BR assay kit (Invitrogen) on a QUBIT™ 3.0 Fluorometer (Invitrogen) and adjusted to 0.2 ng/μl for metagenomic library construction.

Nextera XT libraries were prepared following the manufacturer's protocol (15031942, Illumina). Briefly, samples starting with 1 ng of input DNA were fragmented and tagged via tagmentation, then amplified with a 12-cycle PCR followed by AMPure bead cleanup (A63881, Beckman Coulter). Two technical replicates were generated for each biological sample. Purified amplicons were quantified using QUBIT™ dsDNA HS assay kit (Invitrogen). Samples were pooled at 2 nM each and paired end sequenced (2×150 bp) on an Illumina Nextseq instrument at the Cornell Biotechnology Resource Center Genomics Facility.

Bioinformatics Analysis:

Data quality control: Metagenomic shotgun sequences were dereplicated using the prinseq-lite.pl v0.20.2, with following settings: -derep 12345-no_qual_header. These settings were used to remove exact duplicates (1), 5' duplicates (2), 3' duplicates (3), reverse complement exact duplicates (4), and reverse complement 5'/3' duplicates (5). Dereplicated reads were then passed through the KneadData v0.3 quality control pipeline, which incorporates the Trimmomatic and BMTagger features and decontamination algorithms to remove low-quality reads (thresholding Phred quality score at <20; Minimum length <150) and reads of C57BL/6NJ mouse origin. Taxonomic profiling was performed using MetaPhlAn2. Reads were assembled with IDBA-UD v1.1.1 using the following default settings: --seed_kmer (seed kmer size for alignment)=30, --min_contig (minimum size of contig)=200, --similar (similarity for alignment)=0.95, --min_pairs (minimum number of pairs)=3. Open reading frames were predicted by Prodigal. CD-hit v4.6.1 was used to generate a non-redundant protein database with 100% sequence identity threshold. The protein database was then used to identify linear amide C—N hydrolases/choloylglycine hydrolase family domain proteins, based on Pfam model (PF02275), using HMMER 3 hmmsearch with default settings. The abundance of putative bsh genes are calculated as RPKM (reads per kilobase of the gene per million mapped reads) using outputs from BWA (mem) v0.7.17 and samtools (depth) v1.3.1. Taxonomic assignments for bsh genes were performed using blastp, using DIAMOND v0.9.22.123, of the NCBI-NR database, using default settings and obtaining the unique best hit based on the lowest e-value.

To construct the phylogenetic tree, Clustal Omega v1.2.0 was used to align and generate similarity matrix for proteins identified as putative BSH proteins. A neighbor-joining tree with nearest-neighbor interchange was estimated by FastTree v2.1.7 using default settings. The phylogenic tree was plotted using the Interactive Tree of Life program. Bootstrap confidence levels reflect 100 phylogenetic tree reconstructions.

Code availability: Codes were used from commercial or public sources without modification as indicated above.

Data availability: Raw sequences will be submitted to the NCBI Short Read Archive upon manuscript acceptance.

Identification of bile acid metabolites by mass spectrometry-based metabolomics: Mouse fecal pellets were collected in pre-tared 1.5 mL microfuge tubes as described above. The pellets were lyophilized, weighed, and transferred to a 2 mL microfuge tube, after which the pellets were crushed with a glass rod. Cold methanol (500 μL) was added, and the samples were agitated in a bead beater for 45 s. The samples were chilled on ice for 5 min and centrifuged at 10,000×g for 20 min at 4° C. The supernatant (250 μL) was transferred to a 1.5 ml, microfuge tube and centrifuged under reduced pressure for 2 h. The dried samples were resuspended in 150 μL of LCMS grade MeOH and filtered with a Millex-LH syringe filter equipped with a 0.45 μm PTFE membrane prior to LCMS analysis.

LCMS analysis was performed on an Agilent 6230 electrospray ionization-time-of-flight (ESI-TOF) MS coupled to an Agilent 1260 HPLC equipped with an Agilent Poroshell 120 ECC 18 reverse phase column (3×50 mm, 2.7 μm) using a flow rate of 0.4 mL/min. The water, 0.1% trifluoroacetic acid (ITA):acetonitrile, 0.1% TEA gradient varied from 80:20 to 70:30 over 1.5 min, after which it ramped up to 0:100 in 4 min and remained at 0:100 for an additional 2 min. For detection, the MS was equipped with a dual ESI source operating in negative mode, acquiring in extended dynamic range from m/z 100-3200 at one spectrum per s; gas temperature: 325° C.; drying gas 10 L/min; nebulizer: 20 psig; fragmentor: 325 V.

Quantification of bile acids was performed by integrating the extracted ion count of the exact masses of the bile acids, which were determined using commercial standards. By comparing these data to standard curves in which known amounts of metabolite were injected on the LCMS, the abundance of each metabolite in the samples was quantified and normalized the amounts by the weight of the lyophilized fecal pellets.

Statistics: Each experiment was carried out at least three independent times as indicated. Error bars represent standard deviation from the mean. For box plots, interquartile ranges (IQRs, boxes), median values (line within box), whiskers (lowest and highest values within 1.5 times IQR from the first and third quartiles), and outliers beyond whiskers (dots), are shown. Statistical analyses were carried Out using the Student's t-test (2-tailed) to calculate p values unless otherwise noted above. Densitometry was performed using ImageJ with normalization to the background.

Results and Discussion

Figure 1E:
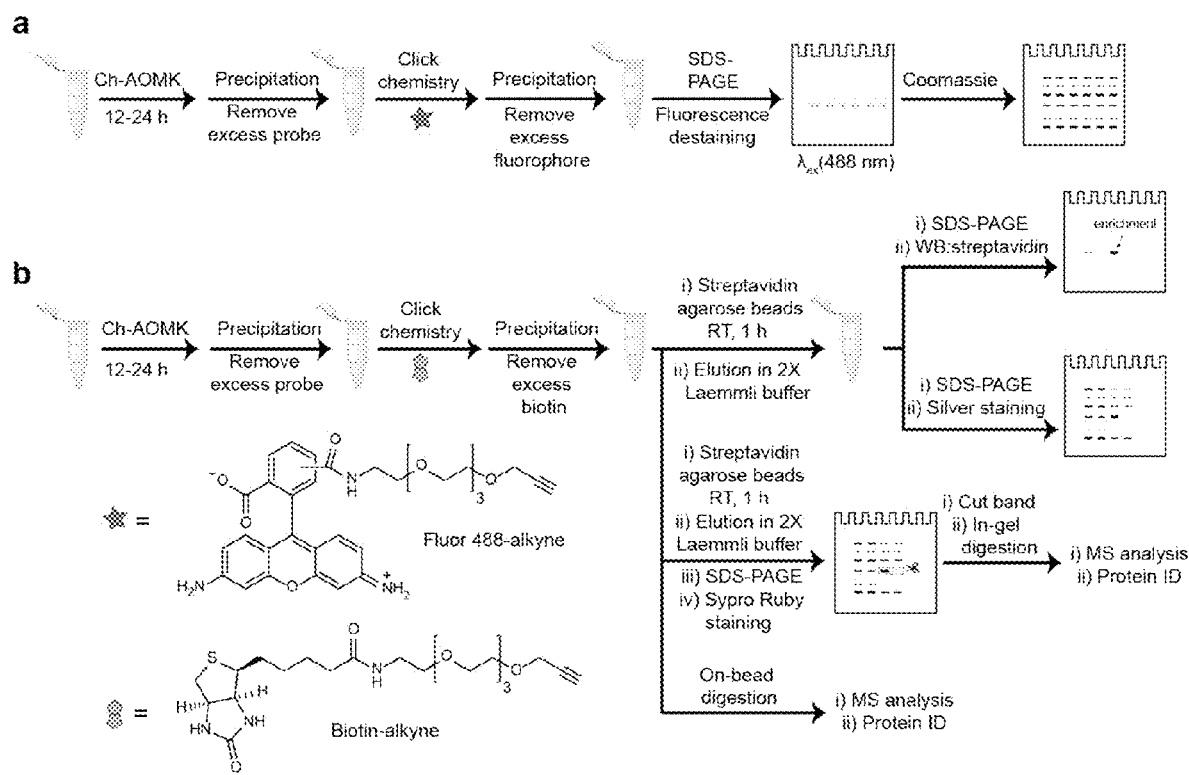

Because BSH is a cysteine hydrolase, the probe (shown in FIGS. 1A-1C) contains an acyloxymethylketone warhead, which selectively labels the active-site nucleophile in this enzyme class. To selectively target the probe to BSHs, the probe was endowed with a cholic acid moiety, because since conjugated cholic acids are substrates of BSHs also known as choloylglycine hydrolases (CGHs) (A. K. Batta. et al., *J. Biol. Chem.*, 259, 24, 15035-15039, 1984). Finally, the probe (named Ch-AOMK for cholic acid-acyloxymethylketone) also contains an azido functional group to permit visualization or enrichment of CGH activity from complex biological samples using CuAAC tagging with either fluorophore- or biotin-conjugated alkynes (FIGS. 1B, 1C, and 1E).

Figures 6A, 6B, 6C:
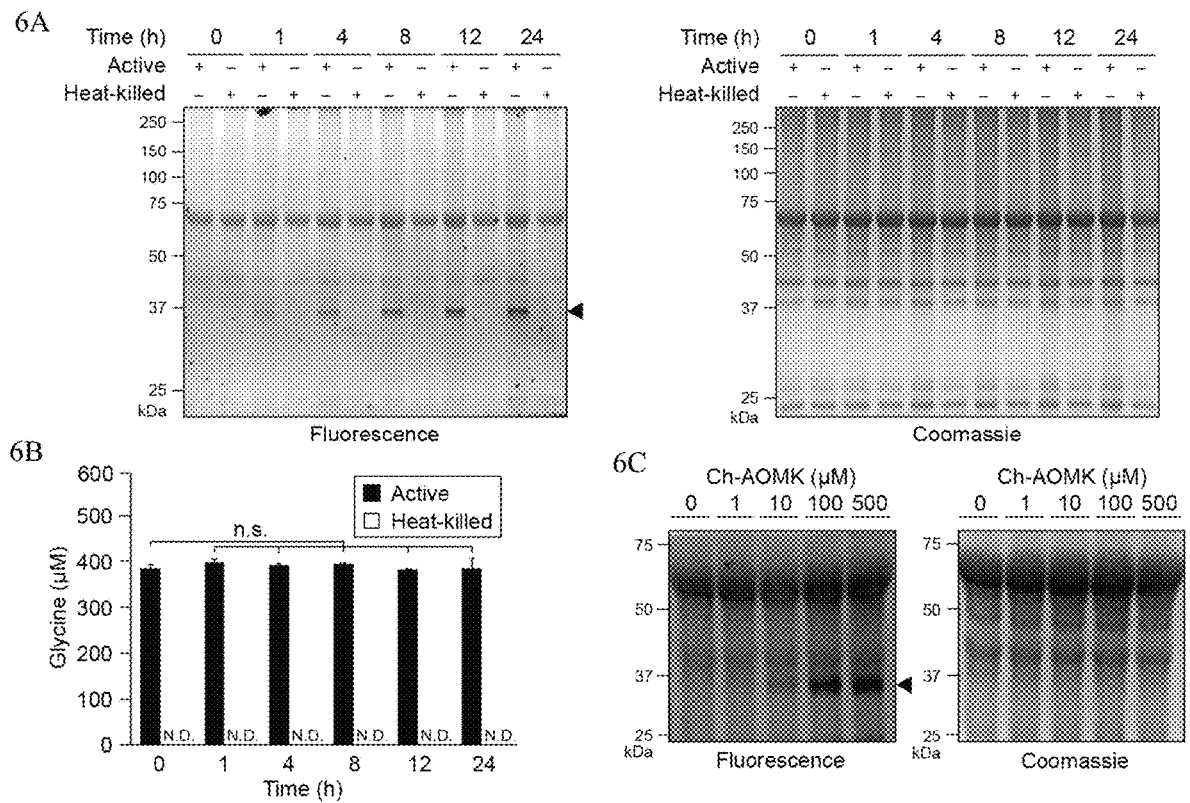
FIGS. 6A-6C. Ch-AOMK labels active *Clostridium perfringens* choloylglycine hydrolase (CGH).

The assay first demonstrated that Ch-AOMK can covalently label active CGH in vitro. In this assay, *Clostridium perfringens* CGH was incubated with Ch-AOMK, followed by CuAAC tagging with a rhodamine 110-alkyne derivative (Fluor 488-alkyne). Analysis of the samples at various times by gel electrophoresis and in-gel fluorescence imaging showed selective labeling of active CGH, but not heat-killed enzyme, with increasing signal over time (FIGS. 2A and 6A). The enzymatic labeling was detectable after 1 hour and reached a maximum at 8 hours. To determine that the enzyme retains activity over this period of time in vitro, a biochemical activity assay was performed under similar reaction conditions with its natural substrate, glycocholate, that measures the release of glycine after enzymatic hydrolysis (FIG. 6B) (C. Bond et al., *J. Biol. Chem.*, 242(1), 7-11, 1967). The assay also demonstrated that increasing the concentration of Ch-AOMK led to a dose-dependent increase in CGH labeling (FIGS. 2B and 6C).

Figures 3A, 3B:
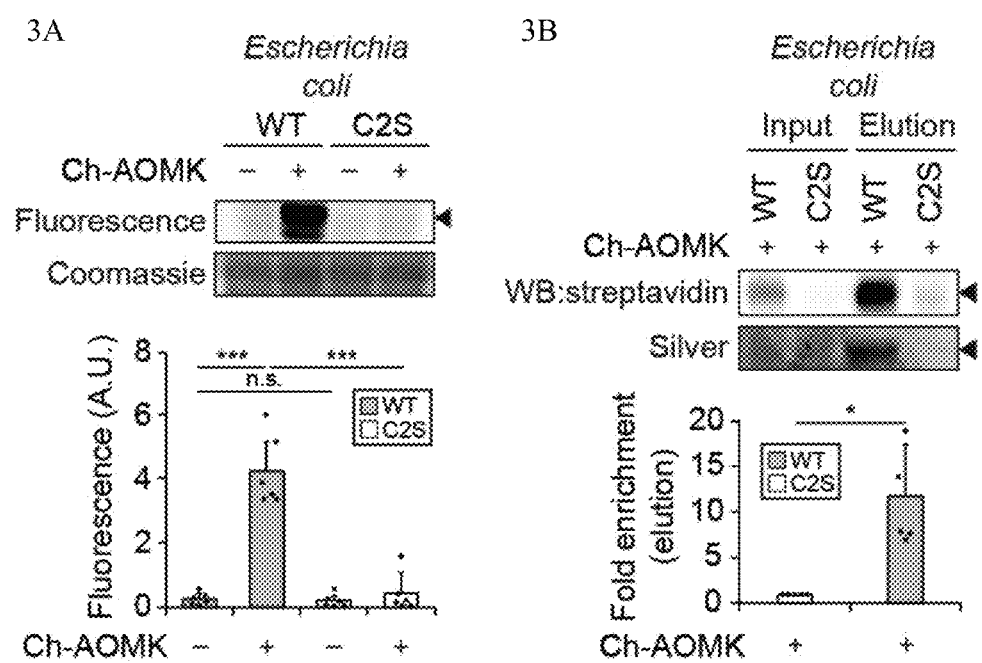
FIGS. 3A-3B. Ch-AOMIK labels *C. perfringens* BSH expressed in *Escherichia coli*. Ch-AOMK (500 µM) was incubated with lysates from *C. perfringens* wildtype (WT) BSH or C2S mutant expressed in *E. coli* at 37° C. for 24 h. Following Ch-AOMK labeling, CuAAC tagging was carried out with Fluor 488-alkyne (FIG. 3A) or biotin-alkyne (FIG. 3B). For FIG. 3A, samples were subjected to SDS-PAGE, and the gel was visualized using fluorescence, followed by Coomassie staining. For FIG. 3B, samples were analyzed either by Western blot with streptavidin-HRP or by silver staining. Input is 2% of the elution. Arrowhead indicates expected size of BSH (37 kDa). A.U.=arbitrary unit. The bands were quantified by densitometry using ImageJ (bottom panels). Error bars represent standard deviation from the mean. * $p<0.05$,  $p<0.01$, * $p<0.001$, n.s.=not significant, n=(a) 6, (b) 5.
Figures 4A, 4B, 4C, 4D:
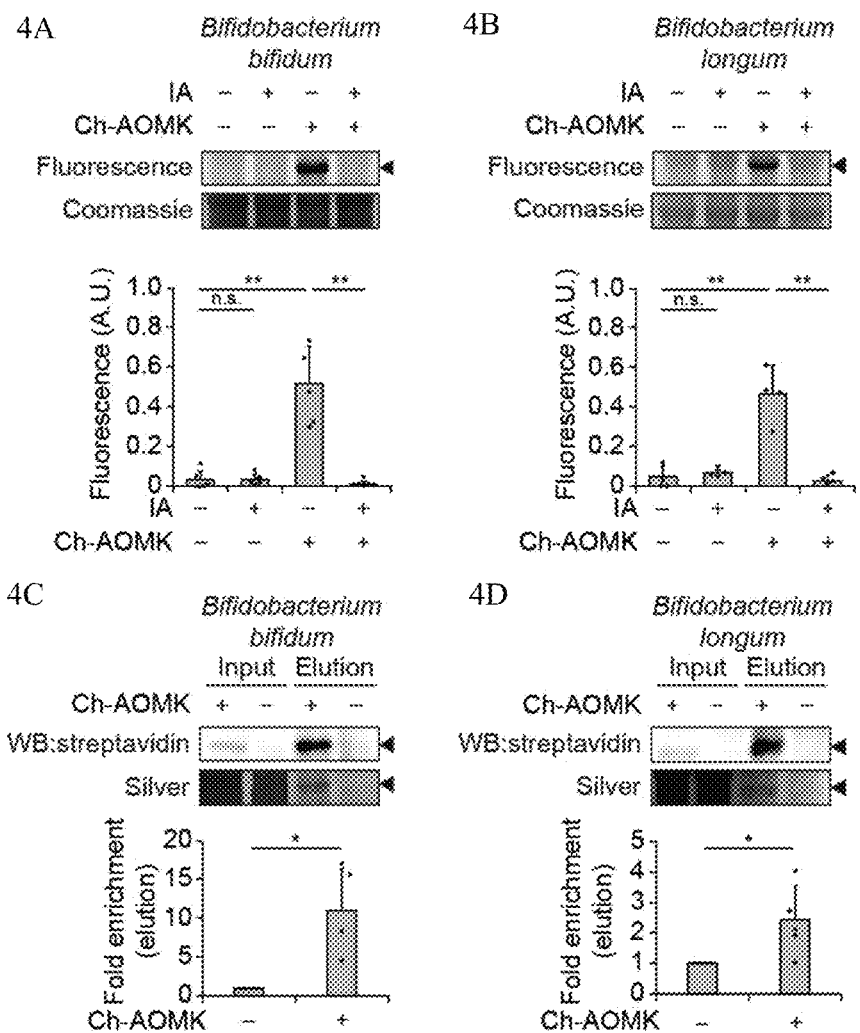
FIGS. 4A-4D. Ch-AOMK labels BSH from gut anaerobes. Ch-AOMK (500 µM) was incubated with lysates from *Bifidobacterium bifidum* (FIGS. 4A, 4C) or *Bifidobacterium longum* (FIGS. 4B, 4D) at 37° C. for 24 h. For FIGS. 4A and 4B, lysates were treated with iodoacetamide (IA, 20 mM) prior to incubation with Ch-AOMK as a negative control. Following Ch-AOMK labeling, CuAAC tagging was carried out with Fluor 488-alkyne (FIGS. 4A-4B) or biotin-alkyne (FIGS. 4C-4D). For FIGS. 4A and 4B, samples were subjected to SDS-PAGE, and the gel was visualized using fluorescence, followed by Coomassie staining. For FIGS. 4C and 4D, samples were analyzed either by Western blot with streptavidin-HRP or by silver staining. Input is 2% of the elution. Arrowhead indicates expected size of BSHs (35 kDa). A.U.=arbitrary unit. The bands were quantified by densitometry using ImageJ (bottom panels). Error bars represent standard deviation from the mean. * $p<0.05$,  $p<0.01$, * $p<0.001$, n.s.=not significant, n=(a) 5, (b) 4, (c) 4, (d) 5.
Figure 7A:
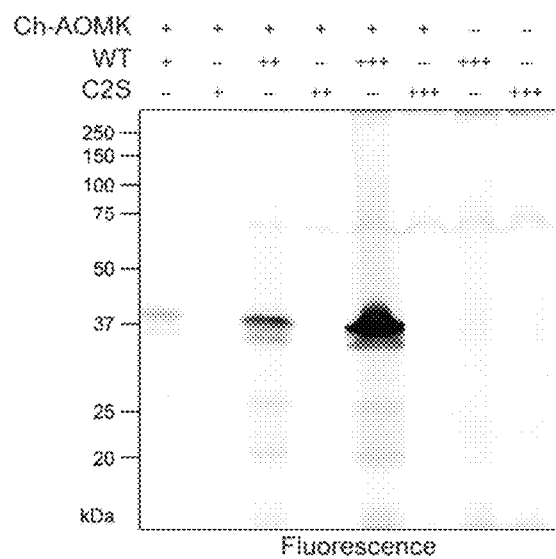
FIGS. 7A-7D. Ch-AOMK labels *C. perfringens* 13A CGH expressed in *E. coli* via the active site cysteine (Cys2). Ch-AOMK (0 or 500 µM) was incubated with increasing amounts of bacterial lysates (50 µg, +; 100 µg, ++; and 250 µg, +++) from *E. coli* expressing either wildtype (WT) CGH or the Cys2Ser (C2S) point mutant at 37° C. After 24 h, the samples were purified by SDS-PAGE and visualized by fluorescence (FIG. 7A), and the gel was subsequently stained with Coomassie brilliant blue (FIG. 7B). Alternatively, the samples were analyzed by Western blot with an anti-FLAG antibody (FIG. 7C), and the blot was stained with Ponceau S as a loading control (FIG. 7D). Arrow indicates CGH at 37 kDa. All bands were quantified by densitometry using ImageJ (a-d, bottom panel). A.U.=arbitrary units. * $p<0.05$,  $p<0.01$, * $p<0.001$, n.s.=not significant, n=5-6.
Figure 7B:
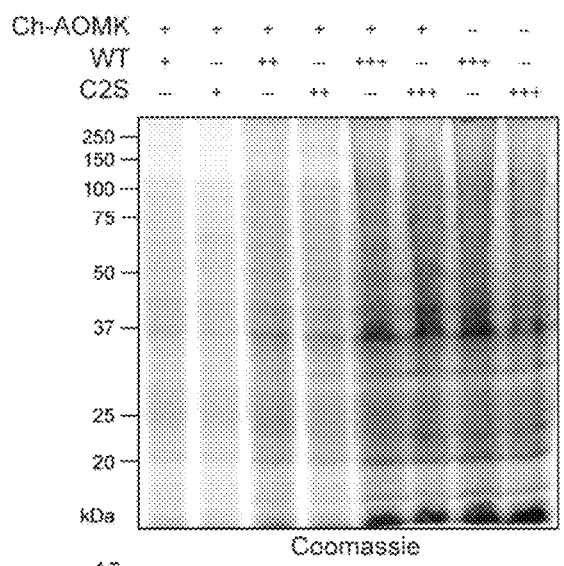
Figure 7C:
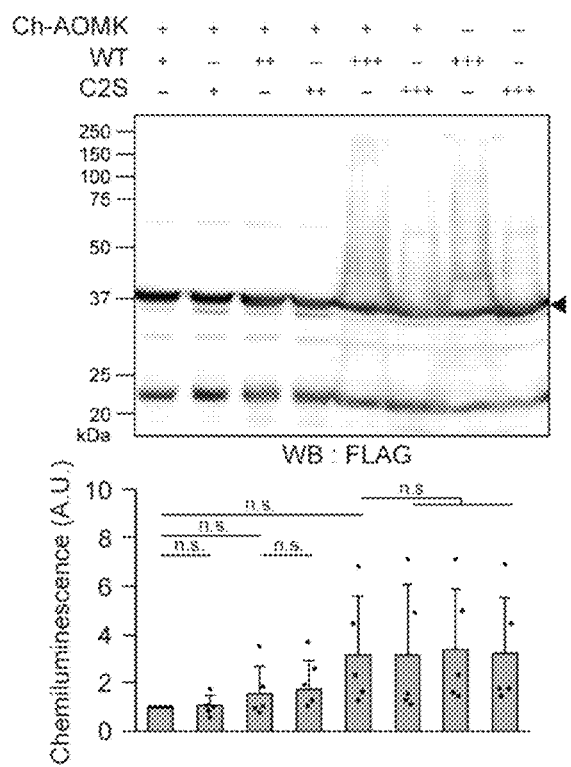
Figure 7D:
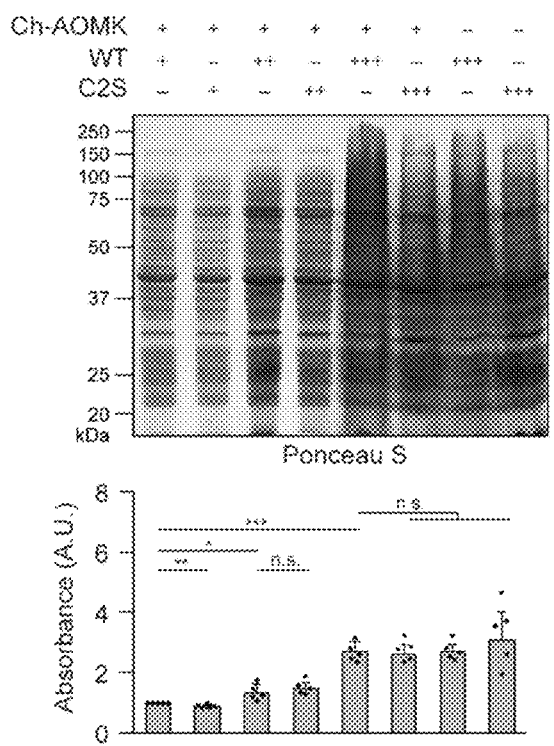
Figures 8A, 8B:
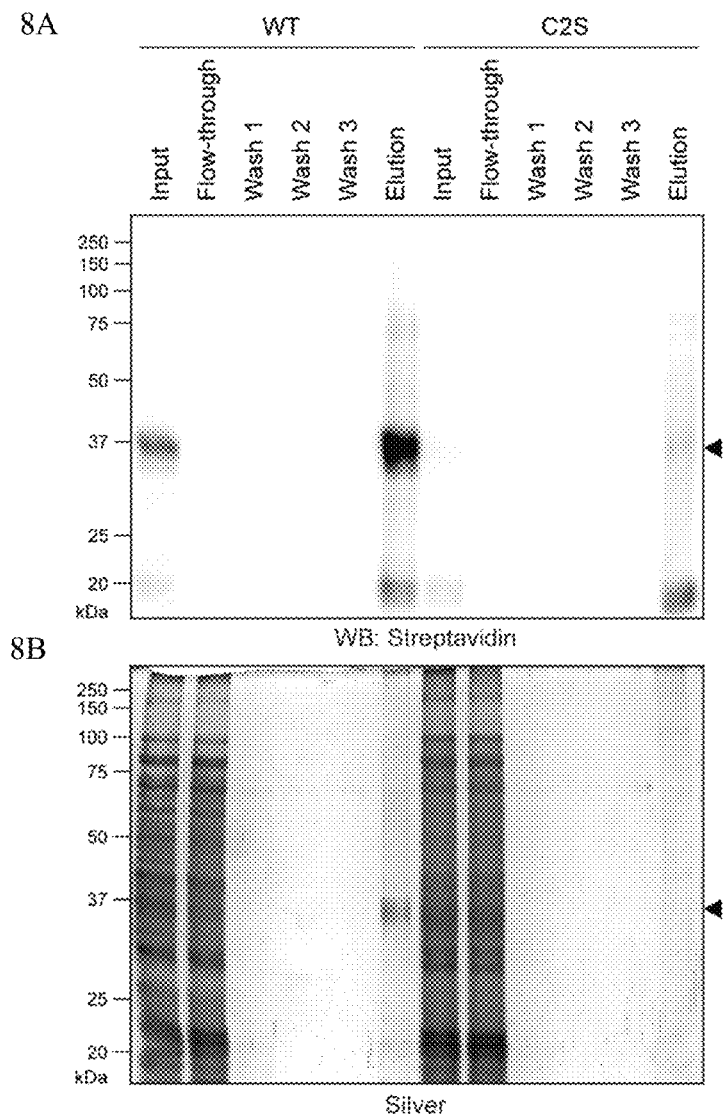
FIGS. 8A-8B. Ch-AOMK labels *C. perfringens* 13A CGH expressed in *E. coli*, followed by pull-down using CuAAC. Bacterial lysate (2.5 mg) from *E. coli* expressing either wildtype (WT) CGH or C2S point mutant were incubated with 500 µM of Ch-AOMK at 37° C. for 24 h. Following click chemistry with biotin-alkyne, labeled proteins were pulled down. Shown is lysate (2% of elution) as input. The samples were analyzed by Western blot with streptavidin-HRP (FIG. 8A) and silver staining as a loading control (FIG. 8B). Arrow indicates CGH at 37 kDa.
Figures 9A, 9B, 9C:
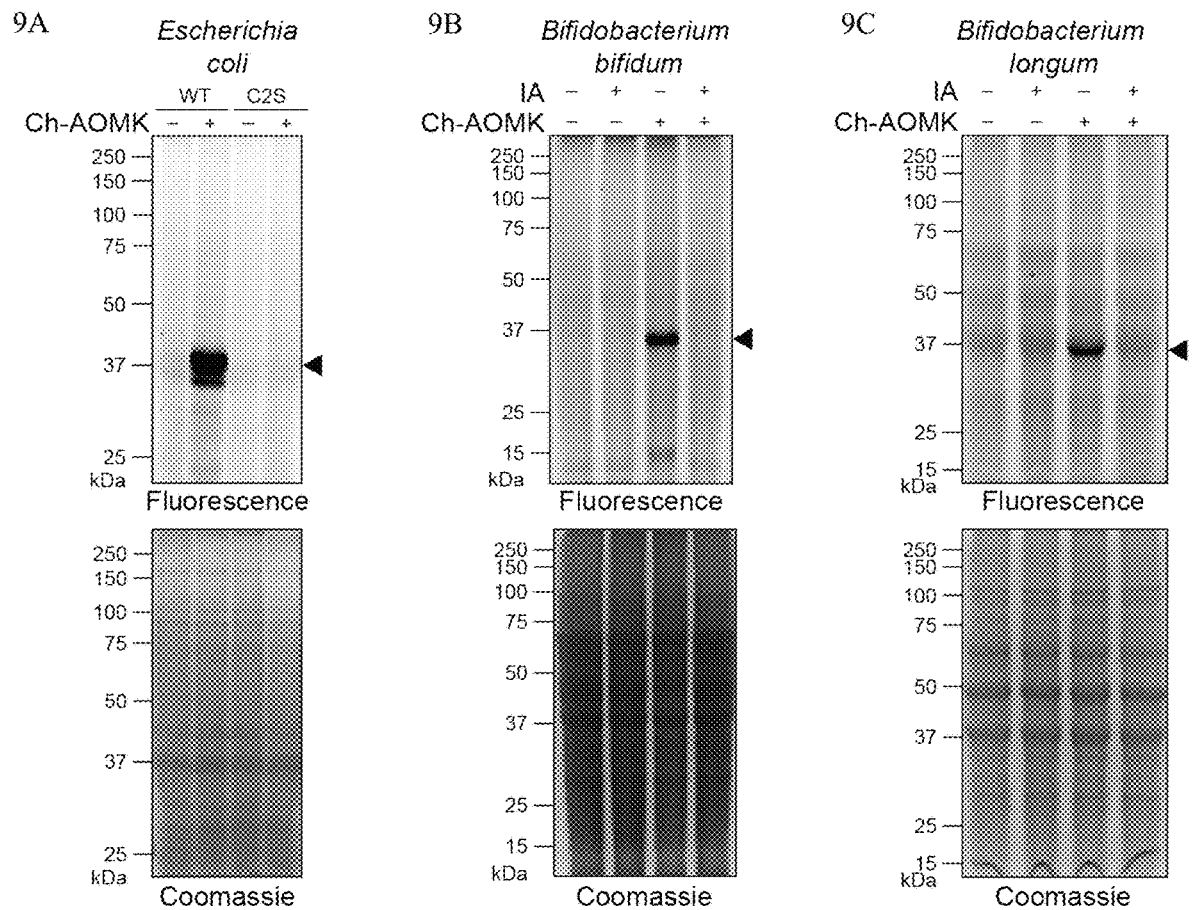
FIGS. 9A-9F. Ch-AOMK labels CGH or BSHs in various bacteria, including gut anaerobes. Ch-AOMK (500 µM) was incubated with lysates from *C. perfringens* WT CGH or C2S mutant expressed in *E. coli* (FIGS. 9A, 9D), *B. bifidum* (FIGS. 9B, 9E), or *B. longum* (FIGS. 9C, 9F) at 37° C. for 24 h. Lysates were treated with or without 20 mM of iodoacetamide (IA) prior to incubation with Ch-AOMK as a negative control. Following Ch-AOMK labeling, click chemistry was carried out with Fluor 488-alkyne (FIGS. 9A-9C) or biotin-alkyne (FIGS. 9D-9F). For FIGS. 9A-9C, samples were subjected to SDS-PAGE, and the gel was visualized using fluorescence, followed by staining with Coomassie. (d-f) Alternatively, samples were analyzed by Western blot with streptavidin-HRP and silver staining (FIGS. 9D-9F). Arrow indicates BSH at 35-37 kDa.
Figures 9D, 9E, 9F:
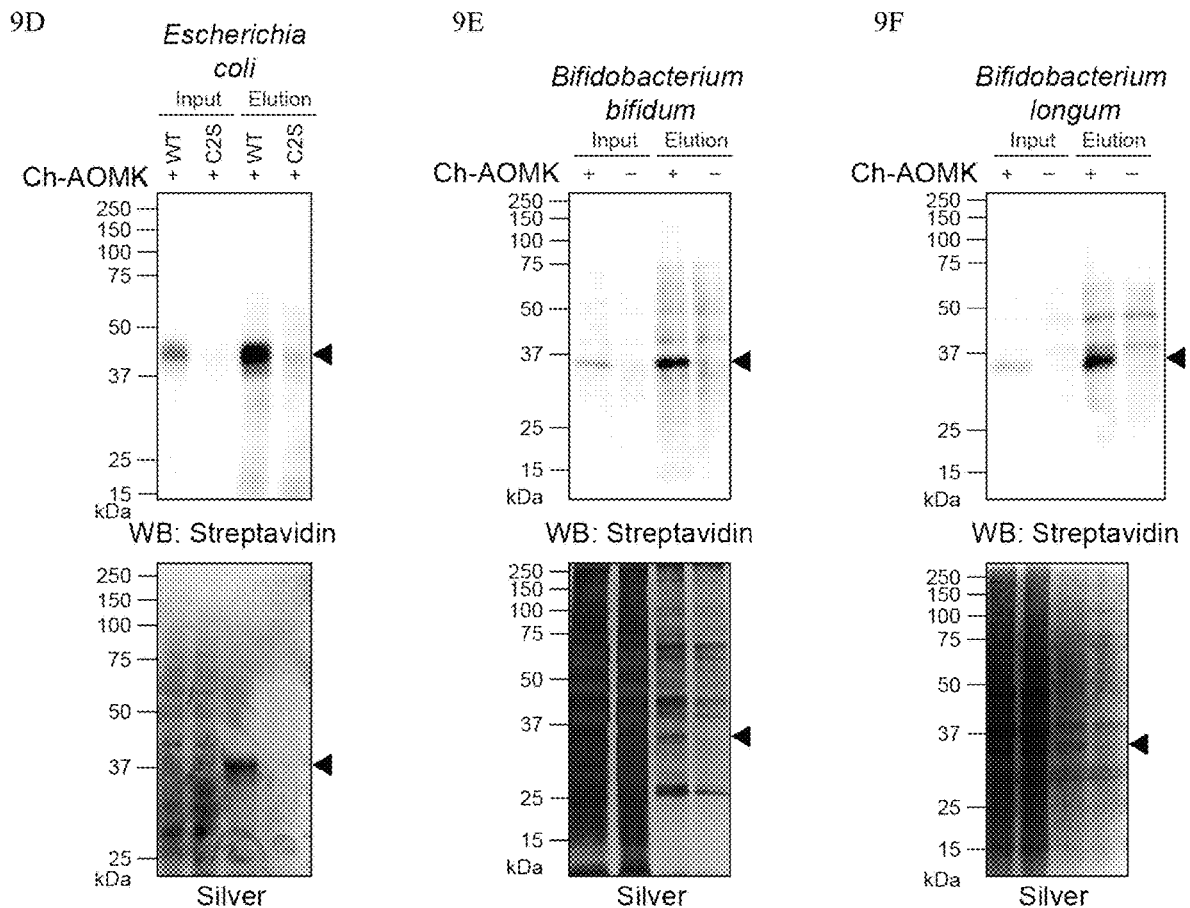

To assess whether Ch-AOMK can selectively label active CGH within bacterial lysates, *C. perfringens* CGH was overexpressed in *Escherichia coli*. It was observed that Ch-AOMK efficiently labeled wildtype (WT) CGH but not the catalytically inactive Cys2Ser (C2S) mutant, using CuAAC tagging with Fluor-488, gel electrophoresis, and in-gel fluorescence imaging (FIGS. 3A, 7A, and 7B). It was also verified that active CGH labeled with Ch-AOMK could be enriched following CuAAC tagging with biotin-alkyne and pull-down using streptavidin-conjugated agarose (FIGS. 3B, 8A, 8B, and 9D). Here, WT and C2S mutant expression were verified by probing for their C-terminal FLAG peptide epitope tag, and importantly, the labeling was dependent on the amount of bacterial lysate (FIGS. 7A-7D).

Further experiments determined that Ch-AOMK can label active BSH within model anaerobic bacterial strains from the gut microbiome whose BSH activities have been biochemically characterized. Lysates generated from *Bifidobacterium bifidum* and *Bifidobacterium longum* were incubated with Ch-AOMK, followed by CuAAC tagging with Fluor 488-alkyne, and samples were analyzed by gel electrophoresis and in-gel fluorescence imaging (FIGS. 4A, 4B, 9B, and 9C). Gratifyingly, Ch-AOMK could facilitate selective visualization of a band with an approximate molecular weight of 35 kDa, the expected size of BSH, from both of these bacteria (R. S. Kumar et al., *J. Biol. Chem.*, 281(43), 32516-32525, 2006). As a control, Ch-AOMK labeling of the 35-kDa species was eliminated in the presence of iodoacetamide (IA), which alkylates cysteine residues and therefore prevents the AOMK warhead from targeting the BSH active-site nucleophile. The *B. bifidium* and *B. longum* BSHs were unequivocally identified as the targets of Ch-AOMK by following the ABP labeling step with CuAAC tagging with biotin-alkyne, streptavidin-agarose enrichment, and identification by mass spectrometry, which verified that the 35-kDa species were indeed BSHs expressed by these bacteria (FIGS. 4C, 4D, 9E, 9F, and Table 1).

Figures 5A, 5B, 5C, 5D:
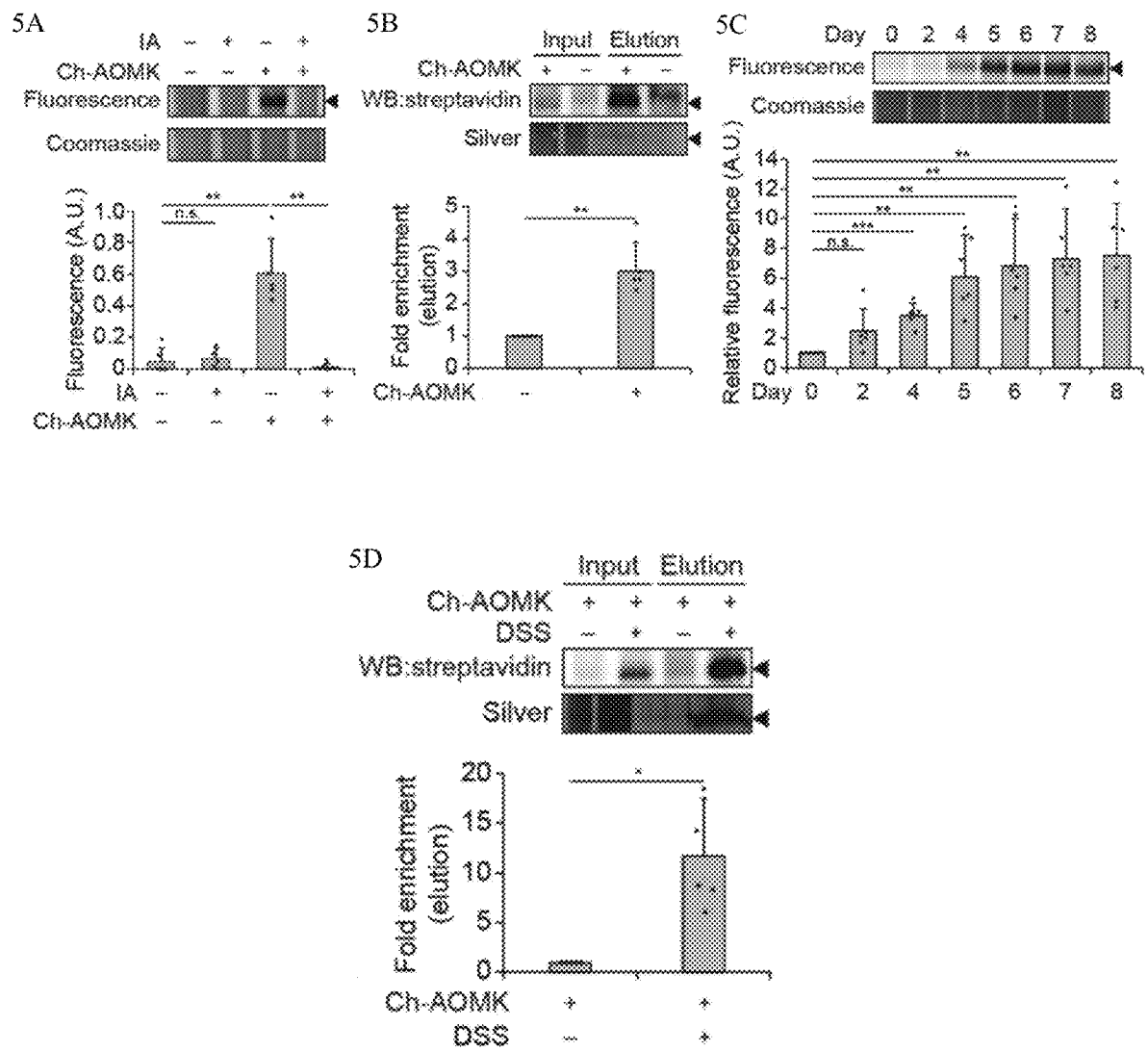
FIGS. 5A-5H. Changes in BSH activity in the gut microbiome are identified using Ch-AOMK in healthy and colitic mice.
Figures 10A, 10B:
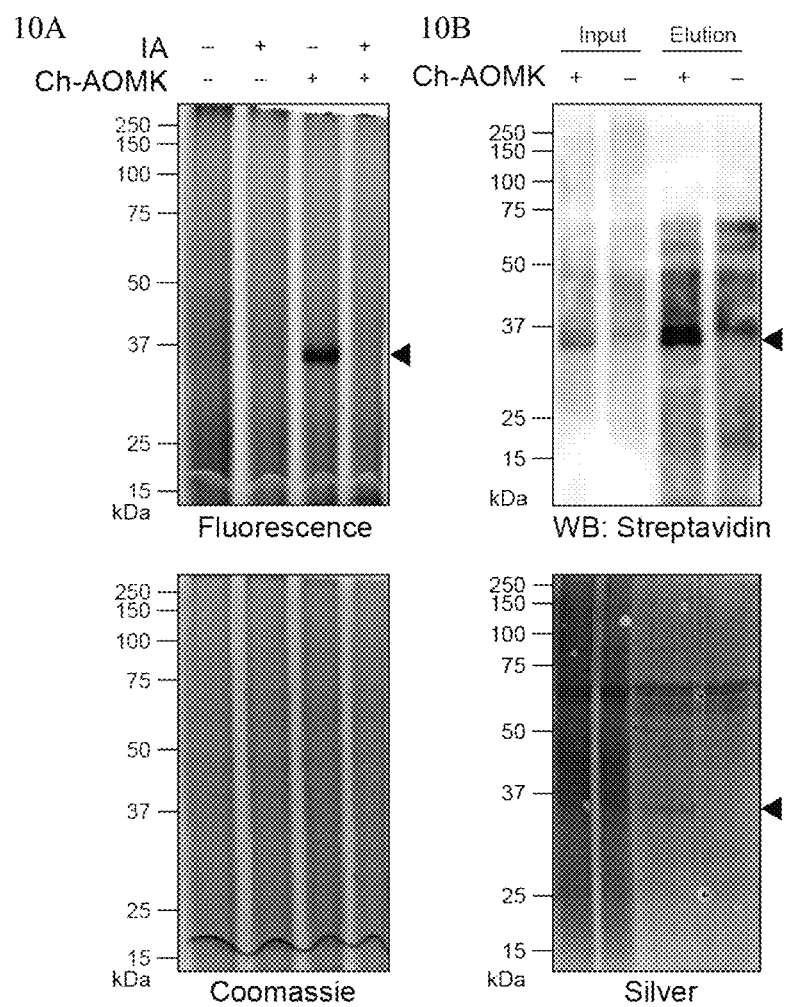
FIGS. 10A-10B. Ch-AOMK labels endogenous BSH in bacteria from the gut microbiome.

To demonstrate that Ch-AOMK can label active BSH within complex biological samples, the ability of Ch-AOMK to target BSH activity was tested within the murine gut microbiome. Lysates from gut bacteria isolated from mouse fecal samples were incubated with Ch-AOMK, followed by CuAAC tagging with Fluor 488-alkyne (FIGS. 5A and 10A). Substantial and selective Ch-AOMK labeling was found in these samples of proteins with approximate molecular weights of 35 kDa, the expected mass of most known gut bacterial BSH enzymes. Ch-AOMK labeling of these species was abrogated by pre-treatment with IA, providing evidence that the labeling is due to covalent reaction with cysteines.

Figure 5E:
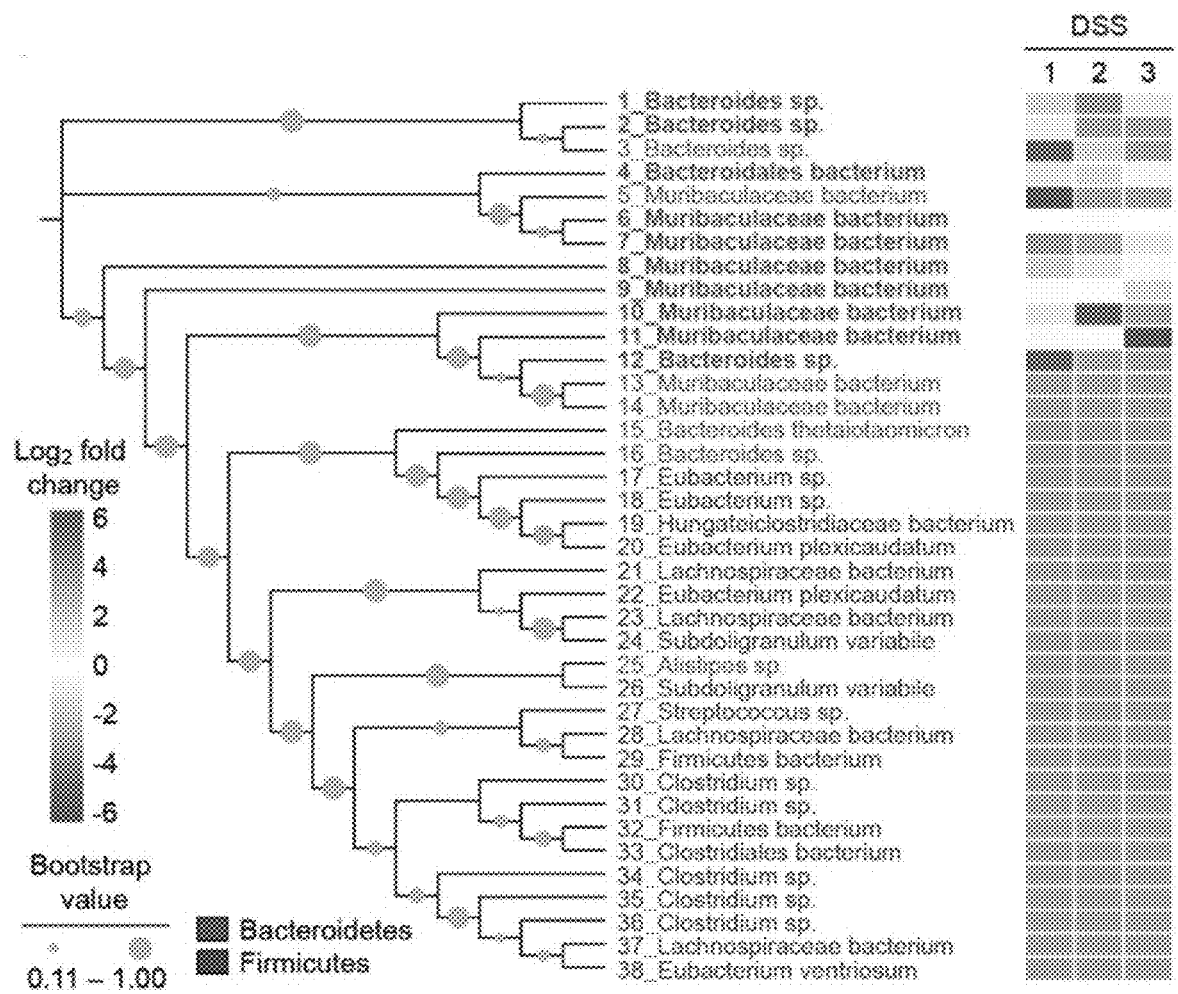
Figures 5F, 5G, 5H:
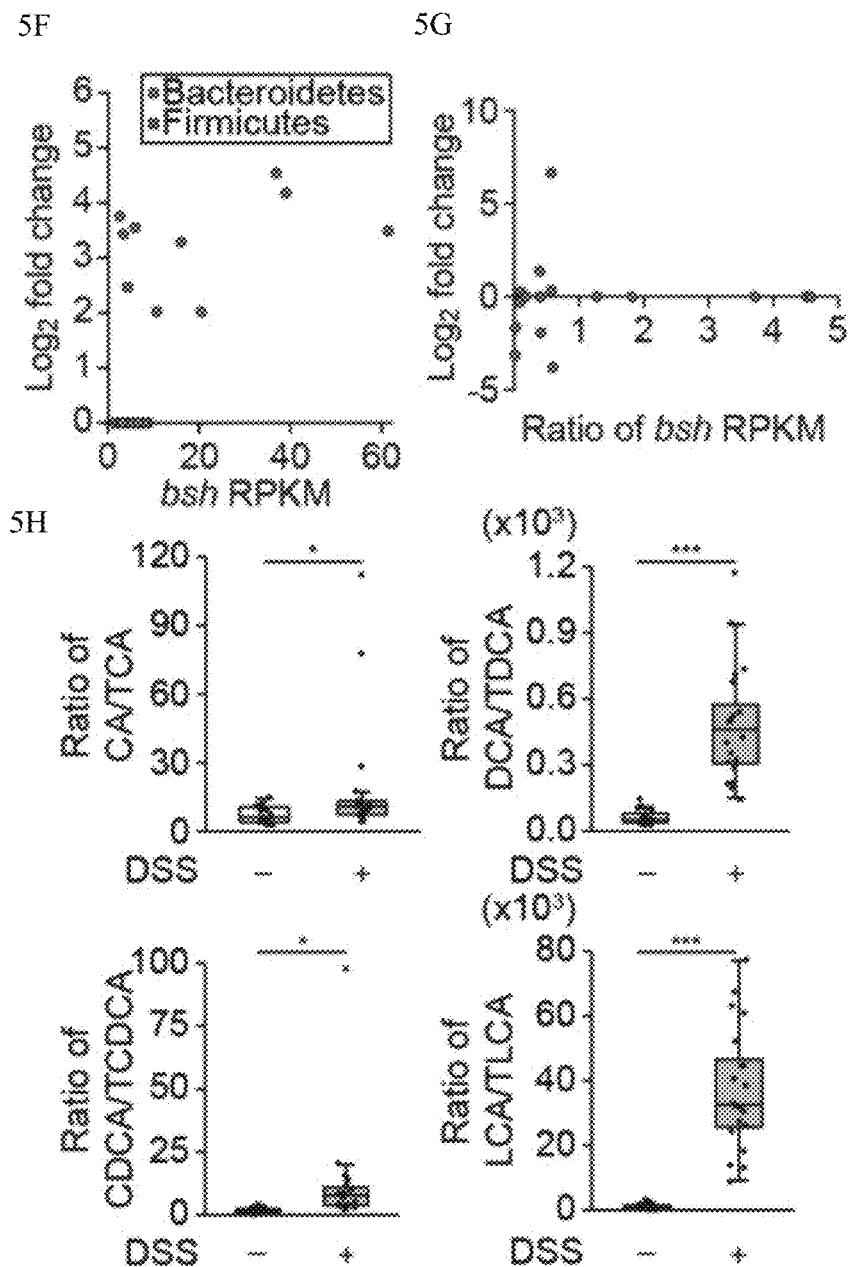
Figure 11:
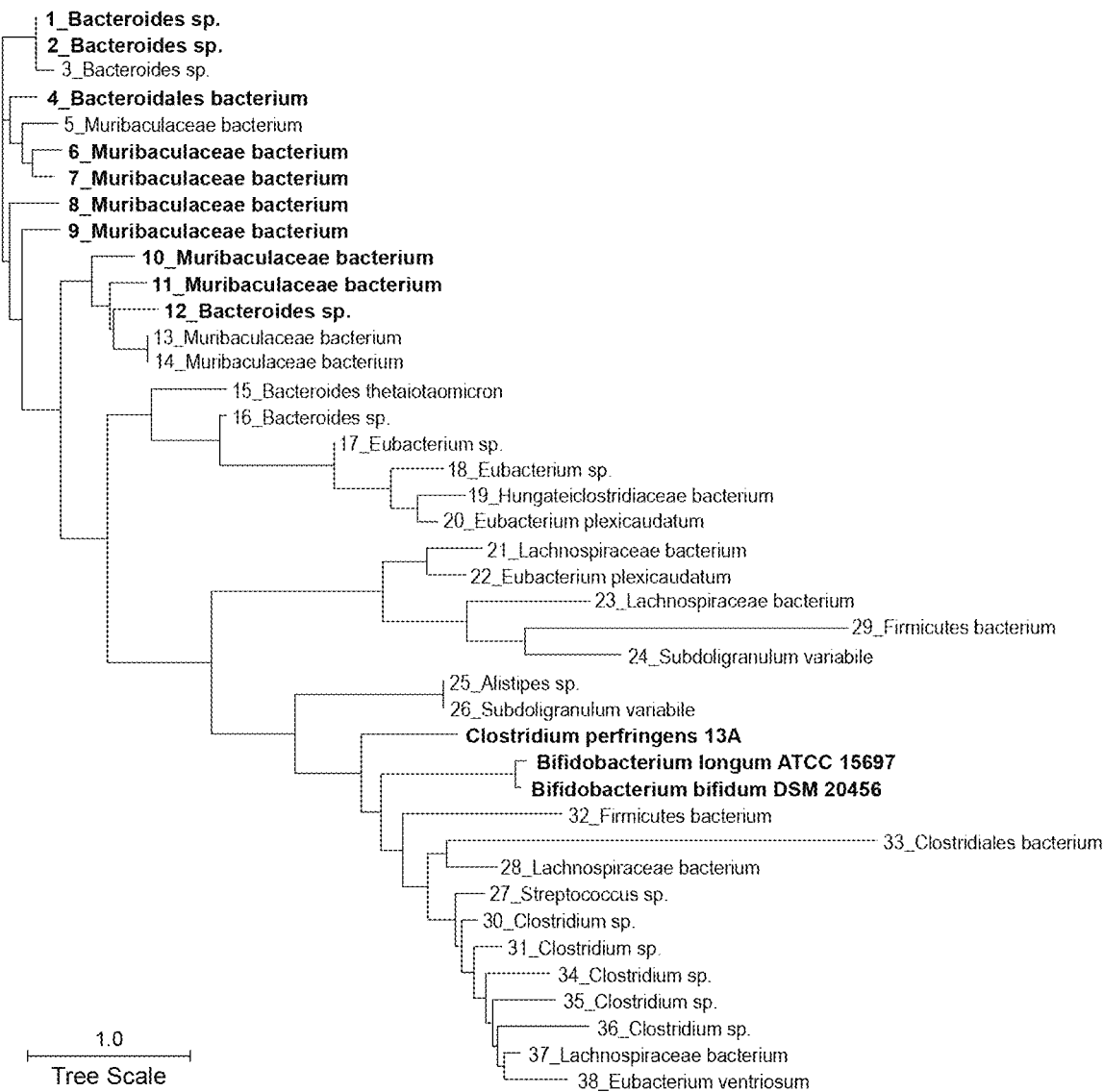
FIG. 11. Phylogenetic tree of putative bile salt hydrolases (BSHs) from bacterial strains that were used in vitro (*C. perfringens, B. bifidum*, and *B. longum*) combined with those identified within the metagenomic assemblies of the mouse gut microbiome. Bacterial BSHs that were identified using the activity-based profiling strategy (i.e., using Ch-AOMK) are shown in bold. Tree scale represents phylogenetic distance, where 1.0=100% sequence identity.

Next, these labeled proteins were identified using MS-based proteomics, following CuAAC with biotin-alkyne and pull-down using streptavidin-agarose, which verified their identities as BSHs (FIGS. 5B and 10B). Although bsh genes are common across phyla, according to the assemblies of shotgun metagenomic sequences from the mouse gut microbiome, the majority of active BSHs within the healthy gut microbiome derived from several bacteria within the phylum Bacteroidetes, which are Gram-negative bacteria that constitute one of the dominant phyla within the gut microbiome (e.g., 20-40% of healthy individuals) and whose BSH activities have recently been biochemically characterized (FIG. 5E) (L. Yao et al., *Elife*, 7, pii: e37182, 2018). To determine whether Ch-AOMK can label BSHs from phylogenetically distant bacteria, the phylogenetic distances were calculated between protein sequences of the active BSHs from the gut microbiome and bacterial BSHs used in the in vitro studies (FIG. 11). From these results, it appears that Ch-AOMK does not have a bias for bacteria from the same taxonomic classification. In addition, Ch-AOMK labeling was not solely dependent on gene abundance because several bacteria within the Bacteroidetes phylum whose bsh genes were at lower abundance exhibited similar enrichment of BSH activity using the chemoproteomics approach to others with more abundant bsh genes. (FIG. 5F).

Figures 12A, 12B, 12C, 12D, 12E, 12F, 12G:
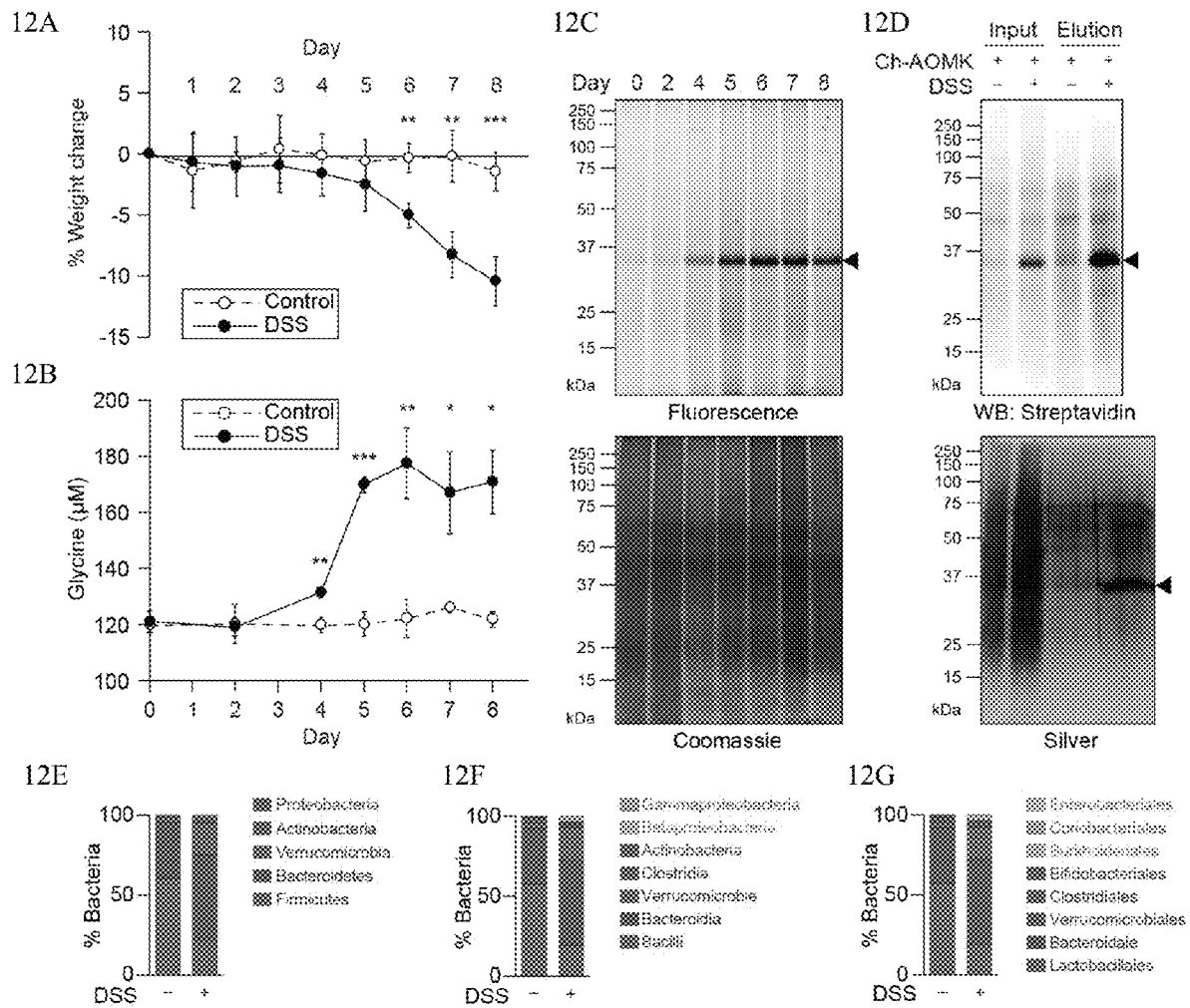
FIGS. 12A-12G. Ch-AOMK labeling reveals that BSH activity is upregulated in dextran sodium sulfate (DSS) colitis. C57Bl/6 mice (n=10-17) were treated with 3% (w/v) DSS (ad libitum) for 8 d, during which their body weights were measured and fecal samples were collected.

Then, a similar strategy was applied to profile BSH activity in IBDs within mice. A well-established mouse model of colitis was used that is induced by treatment with dextran sodium sulfate (DSS), which induces intestinal inflammation resembling the human disease (FIGS. 1A, 12A) (P. M. Munyaka et al., *J. Basic Microbiol.*, 56(9), 986-998, 2016). In these studies, global BSH activity detected by Ch-AOMK labeling increased significantly during DSS treatment, as indicated by CuAAC tagging with Fluor 488-alkyne and in-gel fluorescence (FIGS. 5C and 12C). Additionally, Ch-AOMK labeling, followed by CuAAC with biotin-alkyne and streptavidin-agarose pull-down, led to significantly increased enrichment of BSHs from DSS-treated mice (FIGS. 5D and 12D). Next, it was verified that BSH activity increases during DSS colitis using the biochemical activity assay described above (FIG. 12B). Together, these results suggest that BSH activity increases during DSS colitis in mice.

To examine the individual BSH enzymes contributing to this increase, the enriched samples were analyzed by MS-based proteomics. Unexpectedly, it was found that the overall increase in BSH activity is not due to the activities of specific bacteria because individual bacterial BSHs had altered activities during independent DSS experiments (1-3, FIG. 5E). These data suggest that some bacterial BSH activities increase or decrease, while others remain the same (FIG. 5E), but the global level of BSH activity consistently increases during DSS treatment (FIGS. 5C and 12C). Again, it was found that these changes in BSH activity do not correlate with bsh gene abundance within the gut microbiome metagenomic assemblies (FIG. 5G). These results highlight the dynamic nature of the gut microbiome and the stochastic nature of perturbations to microbial composition that accompany DSS colitis (FIGS. 12E-12G).

Finally, MS-based metabolomics were used to determine whether the increase in global BSH activity leads to changes in levels of relevant primary and secondary BA metabolites. Significantly, it was found that DSS treatment led to increased ratios of deconjugated to conjugated. BAs across four major primary and secondary BAs in the gut, consistent with the Ch-AOMK data indicating increased BSH activity in DSS colitis (FIG. 5H). Thus, it can be concluded that global BSH activity increases in a mouse model of DSS colitis and that this increase is due to the collective BSH activities of the gut microbiome, rather than the activities of specific, individual BSH enzymes.

Other Probes

A series of other probes were synthesized according to the following reaction schemes:

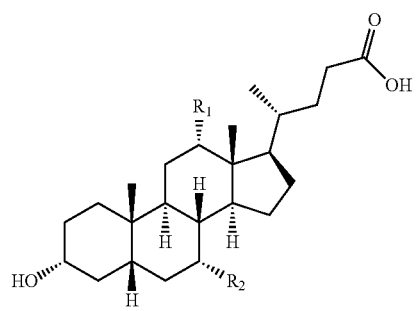

Deoxycholic Acid: R₁ = OH, R₂ = H
Chenodeoxycholic Acid: R₁ = H, R₂ = OH
Lithocholic Acid: R₁ = H, R₂ = H

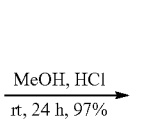

MeOH, HCl
rt, 24 h, 97%

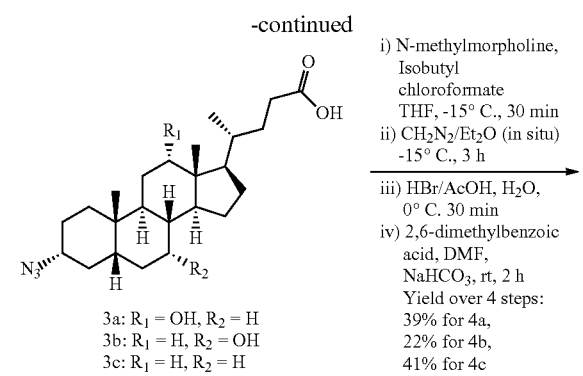

3a: R₁ = OH, R₂ = H
3b: R₁ = H, R₂ = OH
3c: R₁ = H, R₂ = H i) N-methylmorpholine, Isobutyl chloroformate THF, -15° C., 30 min
ii) CH₂N₂/Et₂O (in situ) -15° C., 3 h
iii) HBr/AcOH, H₂O, 0° C. 30 min
iv) 2,6-dimethylbenzoic acid, DMF, NaHCO₃, rt, 2 h
Yield over 4 steps:
39% for 4a,
22% for 4b,
41% for 4c

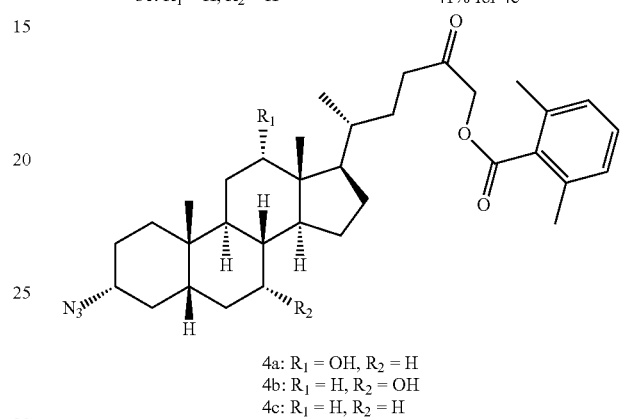

4a: R₁ = OH, R₂ = H
4b: R₁ = H, R₂ = OH
4c: R₁ = H, R₂ = H

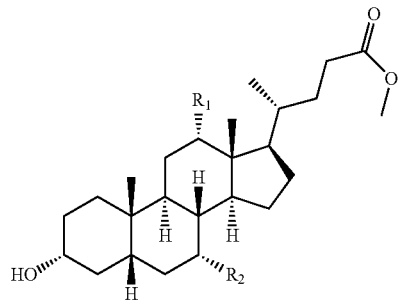

1a: R₁ = OH, R₂ = H
1b: R₁ = H, R₂ = OH
1c: R₁ = H, R₂ = H

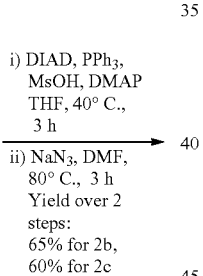

i) DIAD, PPh₃, MsOH, DMAP THF, 40° C., 3 h
ii) NaN₃, DMF, 80° C., 3 h
Yield over 2 steps:
65% for 2b,
60% for 2c

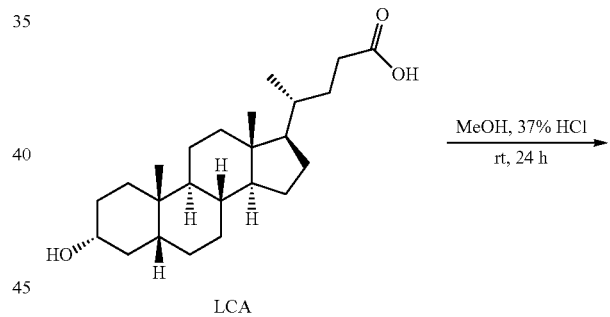

2a: R₁ = OH, R₂ = H
2b: R₁ = H, R₂ = OH
2c: R₁ = H, R₂ = H

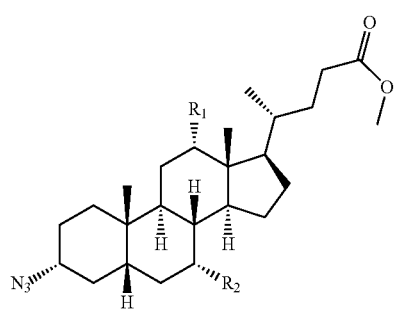

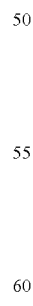

5% aq. KOH
1,4-dioxane,
30 min, 80° C.
80% for 3b
95% for 3c

Compound 1c was synthesized as follows:

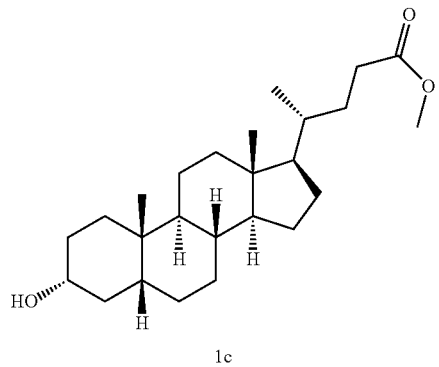

LCA

MeOH, 37% HCl
rt, 24 h

1c

To the solution of lithocholic acid (LCA) (2 g, 5.3 mmol) in MeOH, (50 mL) was added 37% HCl solution (5 mL, 60 mmol). The solution was stirred at room temperature for 24 h. The reaction solution was concentrated in vacuo and neutralized with NaHCO₃ solution. The organic layer was washed with brine, dried over anhydrous Na₂SO₄ and then concentrated in vacuo. The crude was purified by flash column chromatography (Hexane/ethyl acetate=5:1) to provide the purified compound 1c as a white powder. (2 g, 97%).

Compounds 2b and 2c were synthesized as follows:

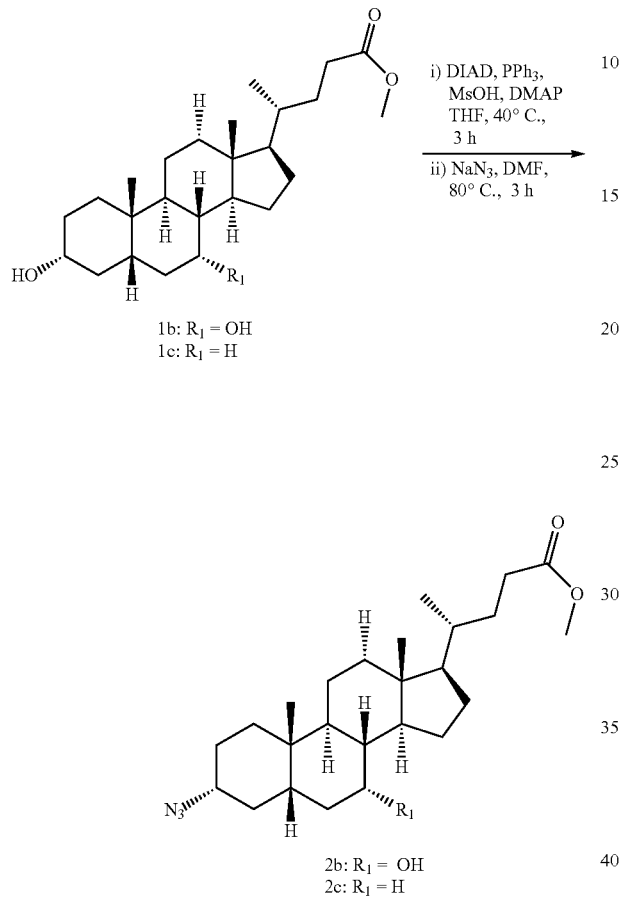

Compound 1b/1c (2.6 mmol) was dissolved in anhydrous THF (10 mL). PPh₃ (7.2 mmol, 2.8 eq.), MsOH (6.1 mmol, 2.4 eq.), and DIAD (7.2 mmol, 2.8 eq.) were added in an inert atmosphere, followed by the addition of DMAP (6.1 mmol, 2.4 eq.). The temperature was raised to 40° C., and the mixture was stirred for 3 h. The reaction mixture was filtered through a sintered funnel containing celite, and the filtrate was concentrated under reduced pressure. This reaction mixture was dissolved in ethyl acetate, washed with 1M HCl, NaHCO₃ and water, dried with anhydrous Na₂SO₄, concentrated in vacuo. The crude was used directly in next step without further purification. Sodium azide (5.2 mmol, 2 eq.) was added under an inert atmosphere to a solution of the crude in anhydrous DMF (10 mL), and the mixture was left stirring at 80° C. for 3 h after which the solvent was removed under reduced pressure. The reaction mixture was dissolved in ethyl acetate, and then washed with water, brine, and dried with anhydrous Na₂SO₄. This organic phase was filtered, concentrated and purified by flash column chromatography (Hexane/ethyl acetate=4:1 for 2b, hexane/ethyl acetate=10:1 for 2c) to provide the purified compound as a colorless crystal 2b/2c, (1.69 mmol, 65% over two steps for 2b; 1.56 mmol, 60% over two steps for 2c).

Compounds 3b and 3c were synthesized as follows:

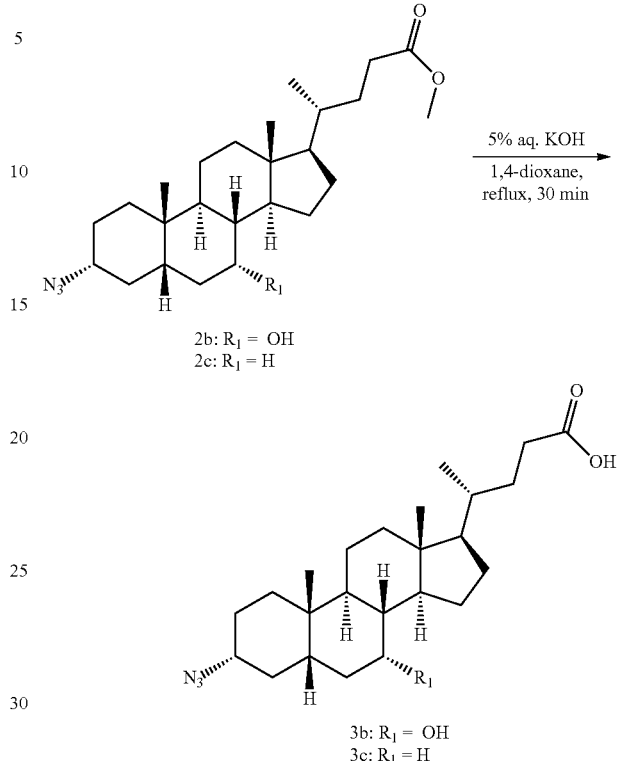

Compound 2b/2c (1.0 mmol) was dissolved in 1,4-dioxane (10 mL), aqueous. KOH (5% w/v, 10 mL) was added, and the mixture was stirred at 80° C. for 30 min. After completion of the reaction, the mixture was concentrated to half the volume under reduced pressure and the aqueous layer was acidified with 1M HCl to a pH of 5-6. Precipitation of the product was observed during the acidification, and the compound was extracted with ethyl acetate (3×30 mL). The combined organic layer was washed with water and dried with anhydrous Na₂SO₄. It was filtered, concentrated, and dried to afford the crude product, which was purified by flash column chromatography (Hexane/ethyl acetate=4:1+1% AcOH for 3b, hexane/ethyl acetate=7:1+1% AcOH for 3c) to provide the purified compound as a colorless oil 3b/3c. (0.8 mmol, 80% for 3b; 0.95 mmol, 95% for 3c).

Compounds 4a, 4b, and 4c were synthesized as follows:

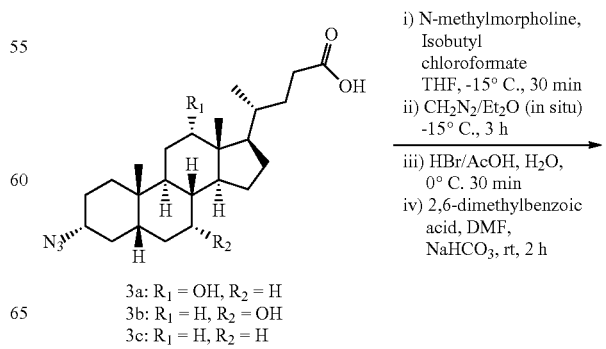

Characterization

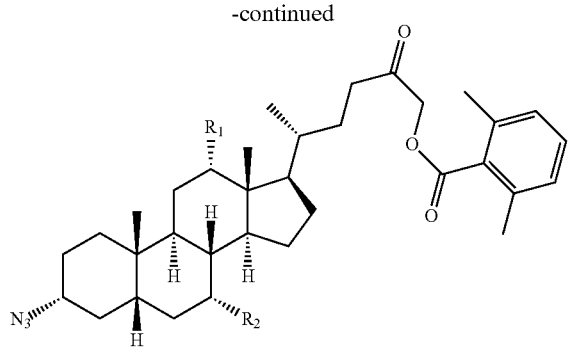

4a: $R_1$ = OH, $R_2$ = H
4b: $R_1$ = H, $R_2$ = OH
4c: $R_1$ = H, $R_2$ = H

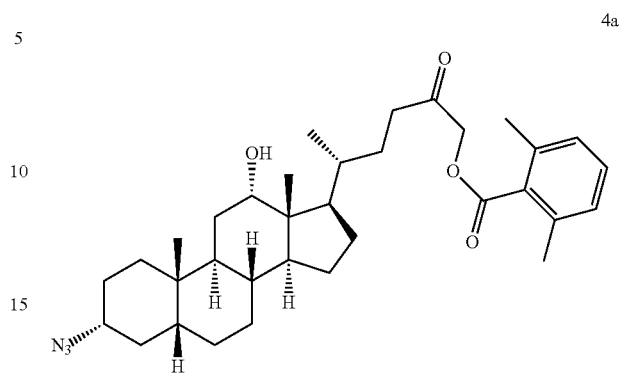

4a

Compound 3a/3b/3c (0.7 mmol) was dissolved in anhydrous THF (3.6 mL) and stirred in a dry ice/acetone bath at −15° C. for 5 min. N-methylmorpholine (98.1 μL, 0.866 mmol, 1.25 eq.) and isobutyl chloroformate (104 μL, 0.8 mmol, 1.15 eq.) were sequentially added to this solution, and the mixture was stirred at −15° C. for an additional 30 min, during which a white precipitate formed. The reaction was brought to 0° C. Ethereal diazomethane was generated in situ according to the procedure reported in the Sigma Aldrich technical bulletin (AL-180). A flame polished glass pipette was used to add diazomethane (3 mmol, 3.75 eq.) dropwise to the reaction mixture at 0° C., and the reaction was slowly warmed to room temperature over 3 h. To generate the corresponding bromomethyl ketone, the reaction mixture was cooled to 0+ C. Hydrogen bromide (33 w % in acetic acid, 5 mL, 75 mmol, 107 eq.) was mixed with 10 mL of water and added to the reaction mixture, dropwise until the evolution of nitrogen gas stopped. The mixture was diluted with ethyl acetate and transferred to a separatory funnel. The organic layer was washed sequentially with water, brine, and $NaHCO_3$, then dried over anhydrous $Na_2SO_4$. The organic layers were combined and rotovapped to yield a sticky yellow solid. The crude was used directly in next steps without further purification. Safety statement: Significant hazards were mitigated in the generation of diazomethane by using ground glass joints, a blast shield, and loosely sealing the reaction vessel. Afterwards, the syringes, needles, and glassware were quenched with acetic acid.

The crude (from 0.7 mmol 3a/3b/3c) was dissolved in dry DMF (0.7 mL) and was stirred at room temperature under nitrogen, and 2,6-dimethylbenzoic acid (30 mg, 0.2 mmol, 0.28 eq.) and $NaHCO_3$ (17 mg, 0.2 mmol, 0.28 eq.) were added. After 2 h, the reaction mixture was diluted with ethyl acetate and transferred to a separatory funnel. The organic layer was washed with water 3 times and dried over anhydrous $Na_2SO_4$. The crude was purified by flash column chromatography (Hexane/ethyl acetate=7:1 for 4a, hexane/ethyl acetate=9:1 for 4b, 4% ethyl acetate in hexane for 4c) to yield a sticky colorless solid. The solid was dissolved in DMSO and further purified by HPLC to generate the purified compound as a colorless oil (0.27 mmol, 39% over 4 steps for 4a; 0.15 mmol, 22% over 4 steps for 4b; 0.29 mmol, 41% over 4 steps for 4c).

$N_3$-DCA-AOMK (4a): $^1$H NMR (500 MHz, DMSO) δ 7.26 (t, J=7.7 Hz, 1H), 7.10 (d, J=7.6 Hz, 2H), 5.03 (s, 2H), 4.19 (d, J=4.3 Hz, 1H), 4.79 (br, 1H), 3.42 (tt, J=11.3, 4.0 Hz, 1H), 2.57-2.37 (m, 2H), 2.31 (s, 6H), 1.85-4.70 (m, 6H), 1.69-1.63 (m,1H), 1.62-1.55 (m, 2H), 1.54-143 (m, 2H), 1.43-1.30 (m, 7H), 1.38-1.15 (m, 3H), 1.11-0.96 (m, 3H), 0.93 (d, J=5.94 Hz, 3H), 0.87 (s, 3H), 0.60 (s, 3H). $^{13}$C NMR (125 MHz, DMSO) δ 204,00, 168.21, 134.67, 132,96, 129.49, 127.48, 71.02, 68,25, 60.36, 47.36, 46.07, 45.97, 41.52, 35,47, 34.90, 34.85, 34.75, 33.68, 32,76, 31.87, 28.82, 28.46, 27.04, 26.56, 26.07, 25.84, 23.39, 22.85, 19.25, 17.04, 12.37. ESI/MS (m/z): [M+Na]$^+$ Calcd: For $C_{34}H_{49}N_3NaO_4^+$: 586.3621; found, 586.3620.

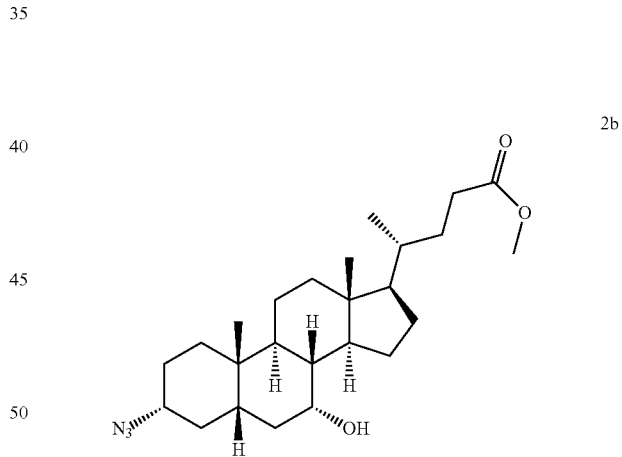

2b $N_3$-CDCA-OMe (2b): $^1$H NMR (500 MHz, DMSO) δ 4.22 (d, J=3.4 Hz, 1H), 3.64 (t, J=3.1 Hz, 1H), 3.57 (s, 3H), 3.23 (tt, J=12.0, 4.2 Hz, 1H), 2.43-2.29 (m, 2H), 2.26-2.17 (m, 1H), 1.96-1.76 (m, 4H), 1.75-1.64 (m, 3H), 1.63-1.55 (m, 2H), 1.46-1.32 (m, 6H), 1.31-1.18 (m, 4H), 1.17-1.08 (m, 2H), 1.06-0.95 (m, 2H), 0.92-0.86 (m, 6H), 0.61 (s, 3H). $^{13}$C NMR (125 MHz, DMSO) δ 173.71, 66.02, 60.68, 55.38, 51,17, 49.91, 41.91, 41.40, 39.23, 35.03, 34.97, 34.89, 34.66, 34.45, 32.23, 30.66, 30.64, 30.33, 27.73, 26.44, 23.08, 22,58, 20.23, 18.10, 11.61. ESI/MS (m/z): [M+Na]$^+$ Calcd: For $C_{25}H_{41}N_3NaO_3^+$: 454.3041; found 454.3461

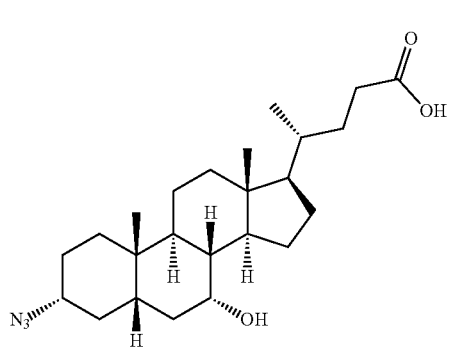

3b

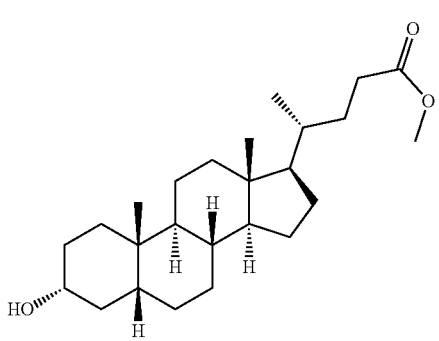

1c

N₃-CDCA-OH (3b): $^1$H NMR (500 MHz, DMSO) δ 11.94 (br, 1H), z4.21 (br, 1H), 3.63 (s, 1H), 3.22 (tt, J=12.0 Hz, 4.3 Hz, 1H), 2.43-2.34 (q, J=12.9 Hz, 1H), 2.26-2.18 (m, 1H), 2.13-2.05 (m, 1H), 1.95-1.76 (m, 4H), 1.73-1.53 (m, 5H), 1.48-1.31 (m, 6H), 1.20-1.05 (m, 6H), 1.03-0.92. (m, 2H), 0.92-0.81 (m, 6H), 0.61 (s, 3H). $^{13}$C NMR (125 MHz, DMSO) δ 174.89, 66.04, 60,70, 55.48, 49.93, 41.92, 41.41, 40,11, 39.26, 35.05, 34.99, 34.93, 34.67, 34.46, 32.24, 30.72, 30.68, 27.77, 26.46, 23.10, 22.60, 20.24, 18.16, 11.65. ESI/MS (m/z): [M-H]⁻ Calcd: For $C_{24}H_{38}N_3O_3^-$: 416.2918; found, 416.2847.

HO-LCA-OMe (1c): R$_f$=0.25 (Hexane/ethyl acetate=3:1), $^1$H NMR (500 MHz, CDCl₃) δ 3.66 (s, 3H), 3.65-3.57 (m, 1H), 2.40-2.31 (m, 1H), 2.25-2.14 (m, 1H), 1.97-1.92 (m, 1H), 1.89-1.78 (m, 3H), 1.78-1.71 (m, 2H), 1.69-1.62 (m, 1H), 1.62-1.53 (m, 1H), 1.53-1.48 (m, 1H), 1.47-1.45 (m, 1H), 1.44-1.35 (m, 6H), 1.34-1.29 (m, 2H), 1.29-1.22 (m, 3H), 1.22-1.15 (m, 1H), 1.14-1.07 (m, 2H), 1.07-1.02 (m, 2H), 1.02-0.92 (m, 1H), 0.90 (d, J=6.7 Hz, 6H), 0.63 (s, 3H). $^{13}$C NMR (125 MHz, CDCl₃) δ 174.75, 71.70, 56.48, 55.94, 51.45, 42.71, 42.10, 40.42, 40.17, 36.40, 35.83, 35.38, 35.34, 34.55, 31.03, 30.98, 30.49, 28,17, 27.20, 26.42, 24.19, 23.37, 20.81, 18.25, 12.02. ESI/MS (m/z): [M+Na]⁺ Calcd: For $C_{25}H_{42}NaO_3^+$: 413.3027; found 413.125.

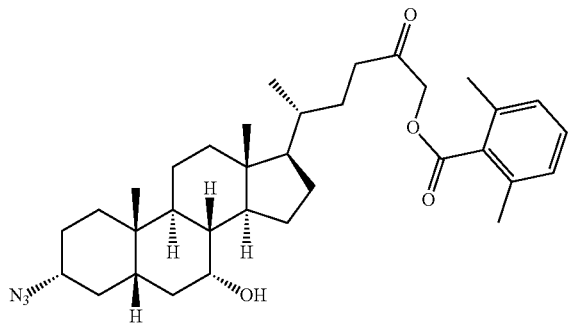

4b

2c

N₃-CDCA-AOMK (4b): R$_f$=0.39 (Hexane/ethyl acetate=4:1), $^1$H NMR (500 MHz, DMSO) δ 7.26 (t, J=7.6 Hz, 1H), 7.11 (d, J=7.6 Hz, 2H), 5.04 (d, J=0.9 Hz, 2H), 4.23 (d, J=3.4 Hz, 1H), 3.64 (p, J=3.1 Hz, 1H), 3.23 (tt, J=11.9, 4.2 Hz, 1H), 2.49-2.34 (m, 2H), 2.31 (s, 6H), 1.96-1.89 (m, 1H), 1.87-1.76 (m, 3H), 1.75-1.64 (m, 3H), 1.63-1.55 (m, 2H), 1.47-1.33 (m, 6H), 1.32-1.19 (m, 4H), 1.18-1.08 (m, 3H), 1.06-0.93 (m, 2H), 0.90 (d, J=6.5 Hz, 3H), 0.87 (s, 3H), 0.62 (s, 3H). $^{13}$C NMR (125 MHz, DMSO) δ 204.00, 168,25, 134.69, 132.99, 129.54, 127.52, 68.29, 66.02, 60.67, 55.38, 49.93, 41.92, 41.37, 39.24, 35.02, 34.97, 34.83, 34.78, 34.66, 34.45, 32.23, 29.58, 28.75, 27.71, 26.43, 23.09, 22.59, 20.22, 19.28, 18.32, 11.66. ESI/MS (m/z): [M+Na]⁺ Calcd: For $C_{34}H_{49}N_3NaO_4^+$: 586.3616; found 586.3333.

N₃-LCA-OMe (2c): $^1$H NMR (500 MHz, CDCl₃) δ 3.66 (s, 3H), 3.31 (tt, J=11.8, 4.4 Hz, 1H), 2.39-2.30 (m, 1H), 2.26-2.16 (m, 1H), 1.98-1.93 (m, 1H), 1.90-1.75 (m, 5H), 1.72-1.65 (m, 1H), 1.60-1.55 (m, 1H), 1.46-1.29 (m, 8H), 1.29-1.21 (m, 3H), 1.19-1.02 (m, 5H), 1.01-0.94 (m, 2H), 0.93 (s, 3H), 0.91 (d, J=6.5 Hz, 3H), 0.64 (s, 3H). $^{13}$C NMR (125 MHz, CDCl₃) δ 174.77, 61.27, 56.40, 55.94, 51.49, 42.73, 42,39, 40.46, 40.08, 35.80, 35.57, 35.38, 34.66, 32.47, 31.06, 31.01, 28.19, 27.10, 26.76, 26.35, 24.20, 23.47, 20.84, 18.28, 12.05. ESI/MS (m/z): [M+N]⁺ Calcd: For $C_{25}H_{41}N_3NaO_2^+$: 438.3091; found 438.3088.

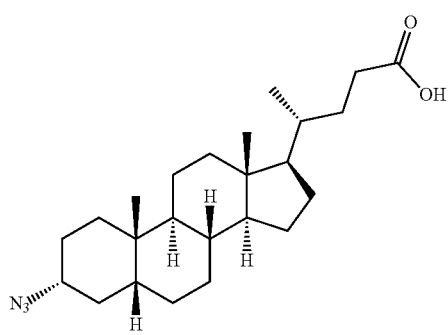

N₃-LCA-OH (3c): $^1$H NMR (500 MHz, CDCl₃) δ 3.35-3.26 (m, 1H), 2.44-2.34 (m, 1H), 2.30-2.21 (m, 1H), 1.99-1.93 (m, 1H), 1.91-1.76 (m, 5H), 1.72-1.65 (m, 1H), 1.61-1.50 (m, 2H), 1.48-1.31 (m, 8H), 1.30-1.21 (m, 3H), 1.20-0.96 (m, 6H), 0.96-0.88 (m, 6H), 0.64 (s, 3H). $^{13}$C NMR (125 MHz, CDCl₃) δ 180.82, 61.27, 56.39, 55.94, 42.75, 42.39, 40.47, 40.08, 35.81, 35.58, 35.32, 34.65, 32.47, 31.10, 30.76, 28.17, 27.11, 26.76, 26.35, 24.19, 23.46, 20.84, 18.26, 12.07. ESI/MS (m/z): [M-H]⁻ Calcd: For $C_{24}H_{38}N_3O_2^-$: 400.2969; found, 400.2926.

N₃-LCA-AOMK (4e): $^1$H NMR (500 MHz, Acetone-d6) δ 7.24 (t, J=7.6 Hz, 1H), 7.09 (d, J=7.0 Hz, 2H), 5.03 (d, J=1.8 Hz, 2H), 3.48-3.35 (m, 1H), 2.69-2.55 (m, 1H), 2.56-2.47 (m, 1 H), 2.37 (s, 6H), 2.03-1.97 (m, 1H), 1.95-1.77 (m, 5H), 1.74-1.66 (m, 1H), 1.63-1.58 (m, 1H), 1.58-1.51 (m,1H), 1.49-1.41 (m, 6H), 1.40-1.34 (m, 2H), 1.34-1.27 (m, 3H), 1.27-1.12 (m, 4H), 1.11-1.04 (m, 2H), 0.98-0.95 (m, 6H), 0.70 (s, 3H). $^{13}$C NMR (12.5 MHz, Acetone) δ 206.13, 204.17, 169.35, 136.14, 134.39, 130.33, 128.41, 68.93, 61.85, 57.19, 56.88, 43.51, 43.12,=11.25, 40.91, 36.68, 36.19, 36.10, 35.98, 35.34, 33.16, 28.83, 27.79, 27.39, 27,12, 24.88, 23.81, 21.58, 19.91, 18.87, 12.44.
$^1$H NMR (500 MHz, CDCl₃) δ 7.21 (t, J=7.6 Hz, 1H), 7.05 (d, J=7.6 Hz, 2H), 4.89 (d, J=2.0 Hz, 2H), 3.36-3.25 (m, 1H), 2.57-2.48 (m, 1H), 2.45-2.36 (m, 7H), 1.99-1.93 (m, 1H), 1.91-1.77 (m, 5H), 1.72-1.66 (m, 1H), 1.60-1.51 (m, 2H), 1.47-1.33 (m, 8H), 1.31-1.21 (m, 5H), 1.20-1.15 (m, 1H), 1.14-1.10 (m, 1H), 1.08-1.00 (m, 3H), 0.94-0.91 (m, 6H), 0.64 (s, 3H). $^{13}$C NMR (125 MHz, CDCl₃) δ 203,89, 169.25, 135.74, 132.85, 129.80, 127.81, 68.24, 61.40, 56.51, 56.01, 42.88, 42.50, 40.58, 40.20, 36.02, 35.92, 35.69, 35.40, 34.78, 32.59, 29.39, 28.33, 27.22, 26.88, 26.46, 24.31, 23.58, 20.96, 20.05, 18.57, 12.20. ESI/MS (m/z): [M+Na]⁺ Calcd: For $C_{34}H_{49}N_3NaO_3^+$: 570.3667; found 570.3666.

FIGS. 13A and 13B show the results of labeling with DCA-AOMK (Compound 4A) and CDCA-AOMK (Compound 4B). As shown, DCA-AOMK and CDCA-AOMK label Clostridium perfringens bile salt hydrolase (BSH). BSH was labeled with varying concentrations (0-500 μM) of DCA-AOMK (FIG. 13A) or CDCA-AOMK (FIG. 13B) at 37° C. for 24 h, after which the samples were tagged using the copper-catalyzed azide-alkyne cycloaddition (CuAAC) with Fluor 488-alkyne. The samples were analyzed by SDS-PAGE and visualized by in-gel fluorescence. A.U.=arbitrary unit. The bands were quantified by densitometry using ImageJ (bottom panels). Error bars represent standard deviation from the mean. * $p<0.05$,  $p<0.01$, * $p<0.001$, n.s.=not significant, n=(A) 3, (B) 5.

While there have been shown and described what are at present considered the preferred embodiments of the invention, those skilled in the art may make various changes and modifications which remain within the scope of the invention defined by the appended claims.

What is claimed is:

1. A compound having the following structure:

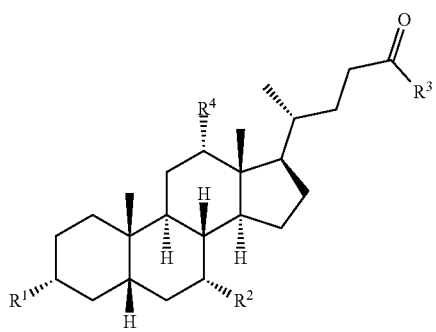

(1)

wherein:
$R^1$ is OH, ester group, ether group, or a group containing an alkynyl or azido functionality;
$R^2$ is H, OH, ester group, ether group, or a group containing an alkynyl or azido functionality;
$R^3$ is a group selected from the group consisting of

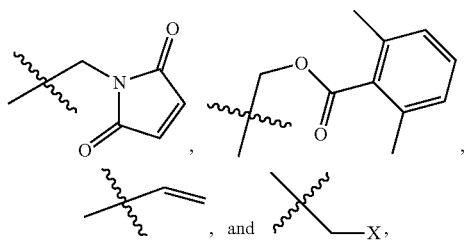

wherein X is a halogen atom; and
$R^4$ is H, OH, ester group, ether group, or a group containing an alkynyl or azido functionality,
wherein one of $R^1$, $R^2$ and $R^4$ is a group containing an alkynyl or azido functionality.

2. The composition of claim 1, wherein $R^1$ is a group containing an alkynyl functionality.

3. The compound of claim 1, wherein $R^1$ is a group containing an azido functionality.

4. The compound of claim 1, wherein $R^2$ and $R^4$ are independently selected from H and OH.

5. The compound of claim 1, wherein $R^2$ and $R^4$ are both OH.

6. The compound of claim 1, wherein $R^3$ is a group containing a reactive functionality capable of covalent binding to a thiol, wherein $R^3$ is selected from

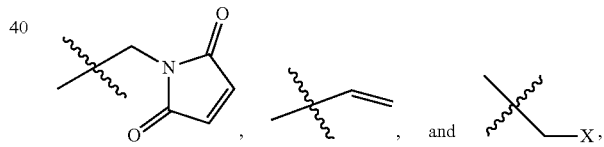

wherein X is a halogen atom.

7. A method for profiling changes in gut microbiome-associated BSH enzyme activity, comprising:
  (i) obtaining a biological sample containing active and inactive BSH enzyme from a mammal;
  (ii) selectively attaching the active BSH enzyme in the obtained sample to a BSH activity-based probe via $R^3$ of the BSH activity-based probe, to provide a probe-BSH enzyme conjugate, wherein the BSH-activity based probe is the compound of claim 1;
  (iii) attaching, by click chemistry, a tagging molecule to an alkynyl or azido group of the BSH activity-based probe after the BSH activity-based probe has attached to the BSH enzyme to form the probe-BSH enzyme conjugate, to result in a tag-BSH enzyme conjugate, wherein the tag permits detection of the active BSH enzyme; and
  (iv) detecting the tag-BSH enzyme conjugate to obtain a BSH enzyme activity profile of the mammal;
wherein the tag-BSH enzyme conjugate produced in step (iii) has the following structure:

(3)

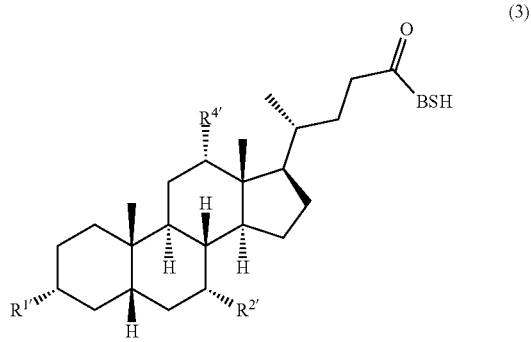

wherein:
$R^{1'}$ is OH, ester group, ether group, or a group $R^a$;
$R^{2'}$ is H, OH, ester group, ether group, or a group $R^a$;
$R^{4'}$ is H, OH, ester group, ether group, or a group $R^a$;
wherein one of $R^{1'}$, $R^{2'}$ and $R^{4'}$ is $R^a$, wherein $R^a$ is

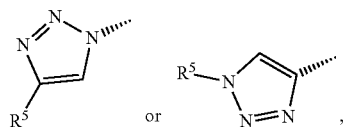

and $R^5$ is said tag that permits detection of the active BSH enzyme.

8. The method of claim 7, wherein the tag-BSH enzyme conjugate produced in step (iii) has the following structure (3a)

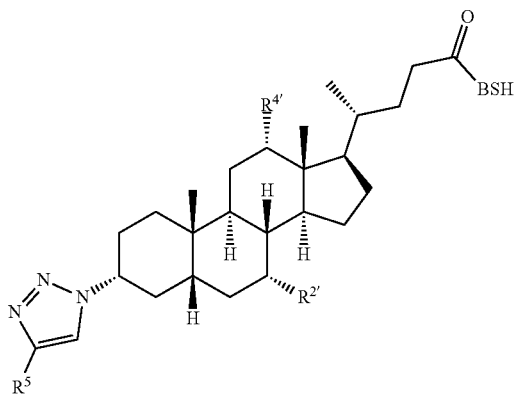

(3b)

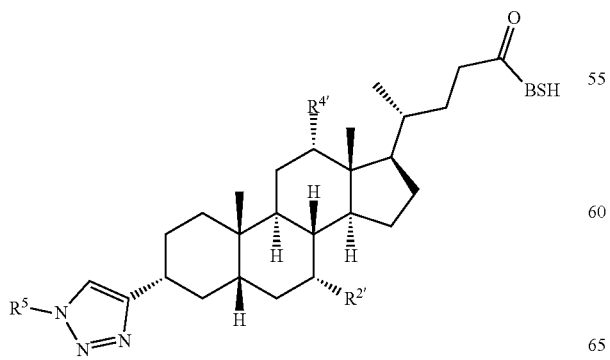

wherein:
$R^{2'}$ is H, OH, ester group, or ether group;
$R^{4'}$ is H, OH, ester group, or ether group; and
$R^5$ is said tag that permits detection of the active BSH enzyme.

9. The method of claim 7, wherein the tag is a fluorophore, metal nanoparticle, or radionuclide.

10. The method of claim 7, wherein the tag is an affinity probe, wherein the affinity probe is a molecule capable of forming an affinity bond with another molecule.

11. The method of claim 10, wherein the affinity probe is selected from the group consisting of biotin, avidin, streptavidin, antigen, and antibody.

12. The method of claim 7, wherein the biological sample is a fecal sample.

13. The method of claim 7, wherein the detecting step (iv) quantifies the amount of labeling to provide a total BSH enzyme activity.

14. The method of claim 7, wherein the detecting step (iv) further comprises identifying the active BSH enzymes that were labeled.

15. The method of claim 14, wherein said identifying is achieved by mass spectroscopy.

16. The method of claim 7, wherein a change in the amount of labeled BSH enzymes compared to a control indicates colitis.

17. The method of claim 7, wherein $R^{2'}$ and $R^{4'}$ are independently selected from H and OH.

18. The method of claim 7, wherein $R^{2'}$ and $R^{4'}$ are both OH.

19. The method of claim 7, wherein, in step (ii), $R^3$ in Formula (1) is a group containing a reactive functionality capable of covalent binding to a thiol, wherein $R^3$ is selected from

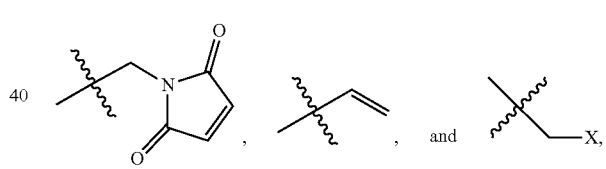

wherein X is a halogen atom.

20. The method of claim 19, wherein said reactive functionality capable of covalent binding to a thiol is selected from the group consisting of a maleimide, acyloxymethylketone, haloacetyl, halomethyl, alkenyl, pyridyl disulfide, and vinylsulfone.

21. The method of claim 7, wherein, in step (ii), $R^3$ in Formula (1) is selected from the group consisting of:

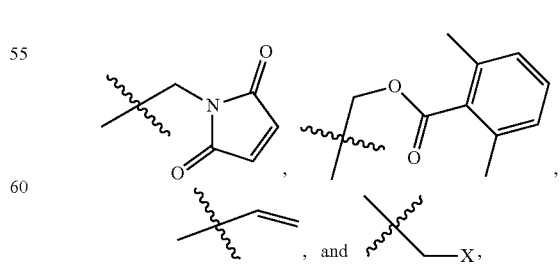

wherein X is a halogen atom.

22. The method of claim 7, wherein step (iv) is a gel-based imaging or affinity-based screening method.

23. The method of claim 7, wherein the method functions as a diagnostic test for colitis in said mammal.

24. The method of claim 23, wherein said colitis is inflammatory bowel disease, ulcerative colitis, or Crohn's disease.

25. The method of claim 7, wherein said mammal is a human.

* * * * *

SEQUENCE LISTING

<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 1
ctagcatatg tgtaccggat tagcgctgga g    31

<210> SEQ ID NO 2
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 2

```
ctagcatatg tctaccggat tagcgctgga gac                           33

<210> SEQ ID NO 3
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 3
ctagctcgag cttatcgtcg tcatccttgt aatcgttcac gtggttgatg ctcag    55

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Asp Tyr Lys Asp Asp Asp Asp Lys
1               5
```